(12) United States Patent
Liu et al.

(10) Patent No.: US 7,509,869 B2
(45) Date of Patent: Mar. 31, 2009

(54) MICROFABRICATED PRESSURE AND SHEAR STRESS SENSORS

(75) Inventors: Chang Liu, Champaign, IL (US); Jack Chen, Urbana, IL (US); Jonathan Engel, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 11/880,134

(22) Filed: Jul. 20, 2007

(65) Prior Publication Data
US 2008/0022778 A1  Jan. 31, 2008

Related U.S. Application Data

(62) Division of application No. 10/861,096, filed on Jun. 4, 2004, now Pat. No. 7,357,035.

(60) Provisional application No. 60/476,672, filed on Jun. 6, 2003.

(51) Int. Cl.
*G01L 7/00* (2006.01)

(52) U.S. Cl. .................................................. 73/756

(58) Field of Classification Search ............. 73/204.26, 73/204.16, 204.11, 204.23, 724, 726, 718
See application file for complete search history.

(56) References Cited

U.S. PATENT DOCUMENTS

| | | |
|---|---|---|
| 4,611,171 A | 9/1986 | Woods |
| 5,239,870 A | 8/1993 | Kaneko |
| 5,412,994 A | 5/1995 | Cook et al. |
| 5,483,834 A * | 1/1996 | Frick ............................ 73/724 |
| 5,726,480 A | 3/1998 | Pister |
| 6,151,771 A | 11/2000 | Tzeng et al. |
| 6,304,840 B1 | 10/2001 | Vance et al. |
| 6,479,890 B1 | 11/2002 | Trieu et al. |
| 6,631,638 B2 * | 10/2003 | James et al. ............. 73/204.26 |

(Continued)

FOREIGN PATENT DOCUMENTS

WO    WO 02095785    11/2002

(Continued)

OTHER PUBLICATIONS

Ayers, J., Zavracky, P.M., McGruener, N., Massa, D., Vorus, V., Mukherjee, R., Currie, S., 1998, "A Modular Behavioral-Based Architecture for Biomimetric Autonomous Underwater Robots," Proc. Autonomous Vehicles in Mine Countermeasures Symp., Naval Postgraduate School, CD ROM, http://www.cix.plym.ac.uk/cis/InsectRobotics/Biomimetics.htm, pp. 1-18.

(Continued)

*Primary Examiner*—Jewel Thompson
(74) *Attorney, Agent, or Firm*—Greer, Burns & Crain, Ltd.

(57) ABSTRACT

A microfabricated pressure sensor. The pressure sensor comprises a raised diaphragm disposed on a substrate. The diaphragm is configured to bend in response to an applied pressure difference. A strain gauge of a conductive material is coupled to a surface of the raised diaphragm and to at least one of the substrate and a piece rigidly connected to the substrate.

18 Claims, 26 Drawing Sheets

U.S. PATENT DOCUMENTS

| 6,825,539 B2 | 11/2004 | Tai et al. |
|---|---|---|
| 2002/0049080 A1 | 4/2002 | Thompson |
| 2002/0060631 A1 | 5/2002 | Runge et al. |

FOREIGN PATENT DOCUMENTS

| WO | WO 03021679 | 3/2003 |
|---|---|---|

OTHER PUBLICATIONS

Barnes, T.G., Truong, T.Q., Lu, X., McGruer, E., Adams, G.G., "Design, Analysis, Fabrication, And Testing of a MEMS Flow Sensor," 1999 ASME International Congress and Exposition on MEMs, vol. 1, 1999, pp. 355-361.

Beebe, D.J., Hsieh, A.S., Denton, D.D., and Radwin, R.G., "A Silicon force Sensor for Robotics and Medicine," Sensors and Actuators, A 50, 1995, pp. 55-65.

Boillat, M. A., van der Wiel, A.J., Hoogerwerf, A.C., de Rooij, N.F., "A Differential Pressure Liquid Flow Sensor for Flow Regulation and dosing Systems," Proc. IEEE Micro Electro Mechanical Systems, 1995, pp. 350-352.

Chen, J., Engel, J., Liu, C., "Development of Polymer-Based Artificial Haircell Using Surface Micromachining and 3D Assembly," 12th Intl. Conf. On Solid-State Sensors, Actuators and Microsystems, Boston, MA, 2003.

Chen, J., Fan, Z., Engel, J., Liu, C., "Towards Modular Integrated Sensors: The Development of Artificial Haircell Sensors Using Efficient Fabrication Methods," Proc. of the 2003 IEEE/RSJ Intl. Conf. On Intelligent Robots and Systems, Las Vegas, NV, Oct. 2003.

Chen, J., Fan, Z., Engel, J., Liu, C., "Two Dimensional Micromachined Flow Sensor Array for Fluid Mechanics Studies," ASCE Journal of Aerospace Engineering, Apr. 2003, pp. 85-97.

Chen, J., Liu, C., "Development and Characterization of Surface Micromachined, Out-of-Plane Hot-Wire Anemometer," Journal of Microelectromechanical Systems, vol. 12, No. 6, Dec. 2003, pp. 979-988.

Chen, J., Zou, J., Liu, C., "A Surface Micromachined, Out-of-Plane Anemometer," Proc of MEMS 02, Las Vegas, NV, 2002, pp. 332-335.

de Bree, H-H, Jansen, H.V., Lammerink, T.S.J., Krijnen, G.J.M, Elwenspoek, m., 1999, "Bi-Directional Fast Flow Sensor with a Large Dynamic Range," J. Micromech. Microeng. 9 (1999), pp. 186-189.

Ebefors, T., Kalvesten, E., Stemme, G., "Three Dimensional Silicon Triple-Hot-Wire Anemometer Based on Polyimide Joints," Proc. 11th Annual Int. Workshop on Micro Electro Mechanical Systems: An Investigation of Micro Structures, Sensor, Actuators, Machines and Systems, Heidelberg, Germany, 1998, pp. 93-98.

Editor, "Touchy Touchy," The Economist, 2002, pp. 66-67.

Engel, J., Chen, J., Liu, C, "Development of a Multi-Modal, Flexible Tactile Sensing Skin Using Polymer Micromachining," 12th Intl. Conf. On Solid-State Sensors, Actuators and Microsystems, Boston, MA, 2003.

Engel, J., Chen, J., Liu, C, "Development of Polyimide Flexible Tactile Sensor Skin," Journal of Micromechanics and Microengineering, vol. 13, No. 9, 2003, pp. 359-366.

Enoksson, P., Stemme, G., Stemme, E., "A Coriolis Mass Flow Sensor Structure in Silicon," Proc. 9th Annual Int. Workshop on Micro Electro Mechanical Systems: An Investigation of Micro Structures, Sensors, Actuators, Machines and Systems, 1996, pp. 156-161.

Fan, Z., Chen, J., Zou, J., Bullen, D., Liu, C., and Delcomyn, F., "Design and Fabrication of Artificial Lateral Line Flow Sensors," Journal of Micromechanics and Microengineering, 12 (Sep. 2002), pp. 655-661.

Gray, B.L., Fearing, R.S., "A Surface Micromachined Microtactile Sensor Array," Proc 1996 IEEE Int'l Conf. On Robotics and Automation, Minneapolis, MN, 1996, pp. 1-6.

Jiang, F., Tai, Y.C., Ho, C.M., Rainer, K., and Garstenauer, M., Theoretical and Experimental Studies of Micromachined Hot-Wire Anemometer, Digest IEEE Int. Electron Devices Meetings (IEDM) (San Francisco), 1994, pp. 139-142.

Jiang, F., Tai, Y.C., Walsh, K., Tsao, T., Lee, G.B., Ho, C.M., "A Flexible MEMS Technology and its First Application to Shear Stress Sensor Skin," Proc 1997 IEEE Int'l Conf. On MEMS, pp. 465-470.

Kalvesten E., Vieider C., Lofdahl, L., Stemme, G., "An Integrated Pressure-Flow Sensor for Correlation Measurements in Turbulent Gas Flows," Sensors Actuators A 52, 1996, pp. 51-58.

Kane, B.J., Cutkosky, M.R., Kovacs, T.A., "A Traction Stress Sensor Array for Use in High-Resolution Robotic Tactile Imaging," Journal of MEMS, vol. 9, 2000, pp. 425-434.

Kolesar, E.S., Dyson, C.S., "Object Imaging with a Piezoelectric Robotic Tactile Sensor," Journal of MEMS, vol. 4, No. 2, 1995, pp. 87-96.

Lee, M.H., Nicholls, H.R., "Tactile Sensing for Mechatronics—a State of the Art Survey," Mechatronics, vol. 9, 1999, pp. 1-33.

Leineweber, M., Pelz, G., Schmidt, M., Kappert, H., Zimmer, G., "New Tactile Sensor Chip with Silicone Rubber Cover," Sensors and Actuators vol. 84, 2000, pp. 236-245.

Liu et al., "Polymer Micromachining and Applications in Sensors, Microfluidics, and Nanotechnology," 226th American Chemical Society National Meeting, New York, 2002.

Li, J., Fan, J., Chen, J., Zou, J, Liu, C., Decomyn, F., "High Yield Microfabrication Process for Biomimetic Artificial Haircell Sensors," smart Electronics, MEMS, and Nanotechnology, Conference (Conference 4700), SPIE's 9th annual International Symposium on Smart Structures and Materials, Mar. 17-21, 2002, San Diego, CA.

Liu, C., Huang, J., Zhu, Z., Jiang, F., Tung, S., Tai, Y.C., Ho, C.M., "A Micromachined Flow Shear-Stress Sensor Based on Thermal Transfer Principles," IEEE/ASME Journal of Microelectromechanical Systems (JMEMS), vol. 8, No. 1, 1999, pp. 90-99.

Lofdahl, L., Kalvesten, E., Hadzianagnostakis, T., Stemme, G., "An Integrated Silicon Based Wall Pressure-Shear Stress Sensor for Measurements in Turbulent Flows," DSC-vol. 59, Proc. 1996 Int. Mechanical Engineering Congress and Exposition, New York, NY, 1996, pp. 245-251.

Lofdahl, L., Stemme, E., Stemme, G., 2001, "Silicon Based Flow Sensors Used for Mean Velocity and Turbulence Measurements," Exp. in Fluids, 12, 1992, pp. 270-276.

Martin, R., "Mother Knows Best: Imitating Nature is the Sincerest Form of Flattery," Forbes ASAP, 2002, pp. 26-29.

Ozaki, Y., Ohyama, T., Yasuda, T., Shimoyama, I., "An Air Flow Sensor Modeled on Wind Receptor Hairs of Insects," Proc. MEMS '00, Miyazaki, Japan, pp. 531-536.

Padmanabhan, A., Goldberg, H., Breuer, K.D., Schmidt, M.A., "A Wafer-Bonded Floating-Element Shear Stress Microsensor with Optical Position Sensing by Photodiodes," J. Microelectromech. Syst., vol. 5, No. 4, 1996, pp. 307-315.

Petersen, "Silicon as a Mechanical Material," Proc of the IEEE, vol. 70, No. 5, 1983, pp. 420-457.

Pfann, W.G., Thurston, R.N., "Semiconducting Stress Transducers Utilizing the Transverse and Shear Piezoresistance Effects," J. Appl., Phys. vol. 32, No. 10, 1961, pp. 2008-2009.

Reston, R.R., Kolesar, E.S., "Robotic Tactile Sensor Array Fabricated from a Piezoelectric Polyvinylidene Fluoride Film," Proc 1990 IEEE NAECON 3, pp. 1139-1144.

Richter, M., Wackerle, M., Woias, P., and Hillerich, B., 1999, "A Novel Flow Sensor with High Time Resolution Based on Differential Pressure Principle," Proc., 12 Int. Conf. On Micro Electro Mechanical Systems (Orlando, FL), pp. 118-123.

Shida, K., Yuji, J.I., "Discrimination of Material Property by Pressure-Conductive Rubber Sheet Sensor with Multi-Sensing Function," Proc 1996 IEEE Int'l Symp. On Industrial Electronics, vol. 1, pp. 54-59.

Shimizu, T., Shikida, M., Sato, K., Itoigawa, K., "A New Type of Tactile Sensor Detecting Contact Force and Hardness of an Object," Proc 2002 IEEE Int'l Conf. On MEMS, 2002, pp. 344-347.

Su et al., "Characterization of a Highly Sensitive Ultra-Thin Piezoresistive Silicon, Cantilever Probe and its Application in Gas Flow Velocity Sensing," Journal of Micromechanics and Microengineering, vol. 12, 2002, pp. 780-785.

Sugiyama, S., Kawahata, K., Yneda, M., Igarashi, I, "Tactile Image Detection Using a 1K-Element Silicon Pressure Sensor Array," Sensors and Actuators A21-A23, 1990, pp. 397-400.

Svedin, N., Kalvesten, E., Stemme, E., Stemme, G., "A New Silicon Gas-Flow Sensor Based on Lift Force," J. Microelectromech. Syst., vol. 7, No. 3, 1998, pp. 303-308.

Svedin, N., Stemme, E., Stemme G., "A Static Turbine Flow Meter with a Micromachined Silicon Torque Sensor," Technical Digest MEMS 2001: 14th IEEE Int. Conf. On Micro Electro Mechanical Systems (Interlaken, Switzerland), 2001, pp. 208-211.

Thaysen et al., "Polymer-based Stress Sensor with Integrated Readout," Journal of Physics D—Applied Physics, vol. 35, No. 21, Nov. 2002, pp. 2698-2703.

van Baar, J.J., Wiegerink, R.J., Iammerink, T.S.J., Krijnen, G.J.M., Elwenspoek, M., "Micromachined Structures for Thermal Measurements of Fluid and Flow Parameters," J. Micromech. Micoeng., 11, 2001, pp. 311-318.

van der Wiel, A.J., Linder, C., Rooij de, N.F., Bezinge, A., 1993, "A Liquid Velocity Sensor Based on the Hot-Wire Principle," Sensors Actuators, A37-A38, pp. 693-697.

van Honschoten, J.W., Krijnen, G.J.M., Svetovoy, V.B., de Bree, H-E, Elwenspoek, M.C., 2001, "Optimization of a Two Wire Thermal Sensor for Flow and Sound Measurements," Proc. 14th Int. Conf. Micro Electro Mechanical Systems (MEMS' 2001), pp. 523-526.

Wang, X., Engel, J., Chen, J., Liu, C., "Liquid Crystal Polymer Based MEMS Applications," Journal of Micromechanics and Microengineering, vol. 13, May 2003, pp. 628-633.

Xu, Y., Jiang, F., Lin, Q., Clendenen, J., Tung, S., and Tai, Y.C., 2002, "Under Water Shear Stress Sensor," MEMS '02: 15th IEEE Int. Conf. On Micro Electro Mechanical Systems, Las Vegas, NV, 2002, pp. 340-343.

Zou, Jun Chen, L., Liu, C., Schutte-aine, J., "Plastic Deformation Magnetic Assembly (PDMA) of Out-of-Plane Microstructures: Technology and Application," Journal of Microelectromechanical Systems, vol. 10, No. 2, 2001, pp. 302-309.

Li, J, Fan, Z., Chen, J., Zou, J., Liu, C., "High Yield Micro Fabrication Process For Biometric Artificial Haircell Sensors," Proceedings of the SPIE-Int. Soc. Opt. Eng USA, vol. 4700, 2002, pp. 315-322.

Shimizu, T., Shikida, M., Sato, K., Itoigawa, K., "Micromachined Active Tactile Sensor for Detecting Contact Force and Hardness of an Object," Oct. 20, 2002, Micromechatronics and Human Science, 2002. Proceedings of 2002 International Symposium, Oct. 20-23, 2002, Piscataway, NJ, USA, IEEE, pp. 67-71.

* cited by examiner

MICROFABRICATED PRESSURE AND SHEAR STRESS SENSORS

PRIORITY CLAIM

The present application is a division of U.S. patent application Ser. No. 10/861,096, filed Jun. 4, 2004, issued as U.S. Pat. No. 7,357,035, which claims the benefit of U.S. Provisional Application Ser. No. 60/476,672, filed Jun. 6, 2003, under 35 U.S.C. §119.

STATEMENT OF GOVERNMENT INTEREST

The invention was made with Government assistance under NSF Grant Nos. IIS-00-80639 and IIS-99-84954, AFOSR Grant F49620-01-1-0496, and NASA Grant No. NAG5-8781. The Government has certain rights in the invention.

FIELD OF THE INVENTION

The invention concerns sensors. The invention relates generally to the field of microscale sensors.

BACKGROUND OF THE INVENTION

Humans and other animals are able to perceive and process environmental conditions using various sensory attributes. For example, animal skin and hair act to provide tactile and flow sensing for perception in land and/or water environments. Man-made devices rely on sensors constructed on many different physical principles, for example heat and resistance, to obtain similar information. Animal sensory systems have attributes that are more elegant and efficient than known sensors.

SUMMARY OF THE INVENTION

Embodiments of the present invention provide, among other things, a microfabricated pressure sensor. The pressure sensor comprises a raised diaphragm disposed on a substrate. The diaphragm is configured to bend in response to an applied pressure difference. A strain gauge of a conductive material is coupled to a surface of the raised diaphragm and to at least one of the substrate and a piece rigidly connected to the substrate.

According to other embodiments of the present invention, a microfabricated shear stress sensor is provided comprising a raised membrane disposed on a substrate and a heated hot-wire element disposed on a surface of the membrane. The heated hot-wire element senses fluid stress.

DETAILED DESCRIPTION

Figure 1:
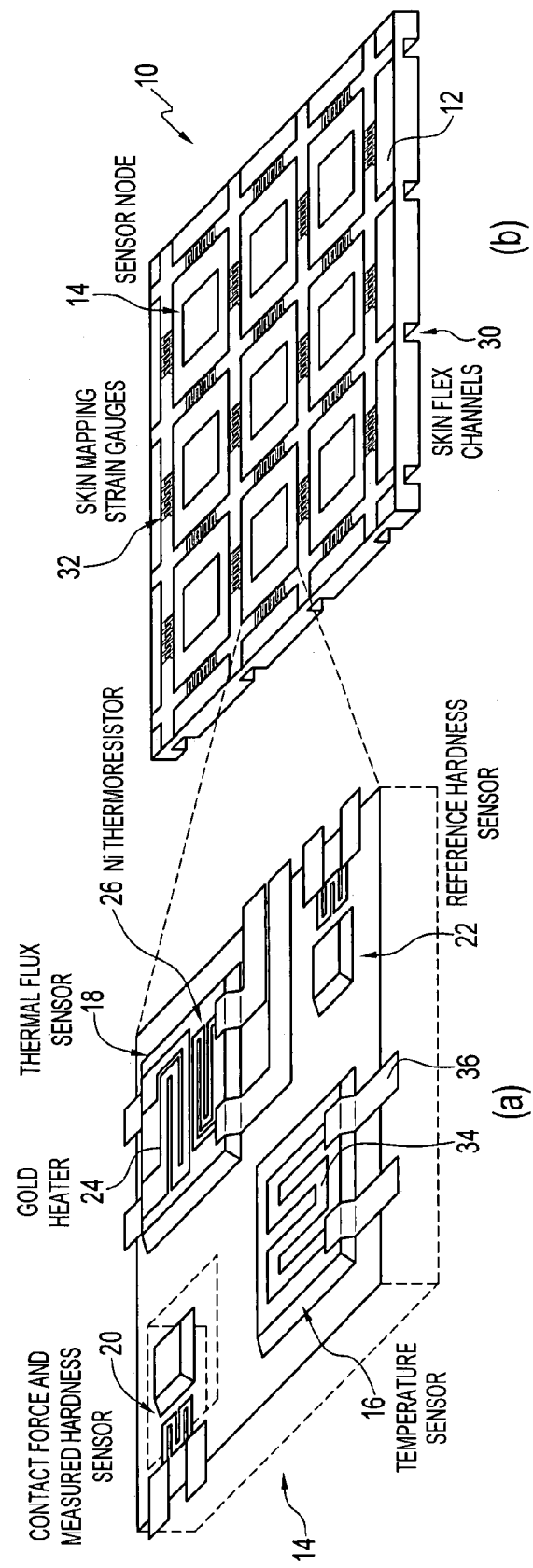
FIG. 1 shows an exemplary tactile sensor node incorporated into a sensor chip, according to a preferred embodiment of the present invention.

For machines such as robotics to replace or serve as extensions of humans in dangerous, delicate, or remote applications, such machines should have sensory input at least comparable to human senses. One of the most important senses for performing varied complex and precise tasks autonomously or remotely is the sense of touch.

Human beings, for example, employ a flexible, robust sensory skin with a distributed architecture to achieve accurate object identification and dexterous manipulation. Tactile feedback from human skin provides a multitude of information, including force, temperature, hardness, texture, and thermal conductivity. However, conventionally, machines have not had the sensing capability to provide an equivalent sense of "touch".

Providing artificial tactile and/or flow sensors that provide rich sensor data incurs significant challenges. For example, an optimal artificial sensor would provide multiple sensing modalities, mechanical flexibility and robustness, efficient signal processing, and high density of integration with signal readout and electronics. Further, it would be preferred that such an artificial sensor would be capable of being manufactured with high efficiency and relatively low cost.

Artificial sensors have been created to provide force imaging and measurement. Such sensors have included silicon-based sensors, using piezoresistive or capacitive sensing, and polymer-based approaches that use piezoelectric polymer films for sensing. Others have combined some of the strengths of silicon with polymer-based devices, such as by embedding silicon sensing elements in polymer skins, or by covering silicon-based devices in a protective polymer layer. Other devices have been used to measure contact force and object thermal properties.

A fundamental difficulty faced in creating artificial sensors such as "sensing skins" is that the sensors in operation would directly contact a variety of objects and contaminants under any number of loading conditions. As a result, devices that incorporate brittle sensing elements such as silicon-based diaphragms or piezoresistors, even embedded in protective polymers, typically cannot be used as an interface "skin" between a robotic manipulator and the manipulated object. Devices made with pressure-sensitive rubbers that can withstand contact have been provided, but they require serial manual assembly and provide limited independent sensing modes.

According to preferred embodiments of the present invention, an artificial sensor chip (or a large-area patch) is provided on a polymer-based substrate, forming a skin. Preferably, the sensor chip is flexible, providing a sensory skin that can be, for example, mounted on curved or other non-flat surfaces easily and can withstand mechanical flexure and movement.

The sensor chip incorporates one or more metal film sensors. This provides many functional advantages and uses. The sensors preferably are distributed in an array, such as a two-dimensional array, having high spatial density and integrated signal processing capabilities. The sensor chip and sensor components thereon preferably are sufficiently robust to survive mechanical contact with an external harsh environment.

Unlike sensors in an integrated circuit chip that are packaged in enclosed environments, individual sensors according to a preferred sensor chip are exposed. Also, it is preferred that a frontal surface of the sensor chip be relatively smooth and free from mechanical protrusions, etch holes, exposed wiring, or other flaws and design compromises that would allow environmental contamination or accelerated wear and failure of the device.

In a preferred sensor chip, the distributed sensors are connected using signal processing circuitry that is distributed spatially and can accommodate multiple streams of analog sensor output with minimal footprint and power. Local, distributed signal amplification and analog-digital conversion are preferred to preserve signal-to-noise ratio (before a signal is broadcasted through wire leads). Local signal processing avoids the routing bottleneck associated with long wire leads.

The density of integration of the sensors on a preferred sensor chip may reach as high as, for example, 1-10/mm$^2$. The maximum density on a preferred chip may be determined not only by sensor sizes but also by the footprint of signal processing circuits.

Also, in preferred methods of manufacturing the sensor chip, the cost of manufacture should be as low as possible to allow widespread use, especially if large continuous sensor chip surfaces are required. Manufacturing processes are preferably integrated and efficient. Particularly, monolithic integration is preferred because costs can be reduced through batch fabrication. It is also preferred that the efforts for calibrating three-dimensional sensor positions should be minimized to streamline their use.

Preferred sensor chips include multi-modal sensor nodes that are for tactile sensing and/or for flow sensing. For example, a multi-modal tactile sensing node may be provided.

A preferred multi-modal tactile sensor node can successfully incorporate multiple sensor modalities for evaluating one or more of contact forces, and the relative hardness, thermal conductivity, and/or temperature of a contacted object.

Traditional microfabricated tactile sensors suffer from a number of significant disadvantages. For example, they are typically based on silicon, which is usually a rigid and fragile material from a mechanical point of view. Exposing the sensors presents problems if silicon is used, because silicon is easy to fracture upon mechanical impact and over-loading. For example, many silicon micromachined tactile sensors do not stand force loading well.

The individual sensors of each multi-modal sensory node are fabricated on the polymer-based substrate using surface micromachining. Thin-film metal elements are used, for example, as piezoresistors, heaters, and temperature sensors. Preferred methods for manufacturing the individual sensors involve a relatively low temperature and do not involve bulk micromachining. In this way, all of the sensors can be formed on the polymer-based substrate.

Also, traditional silicon sensors only sense surface roughness features and contact forces. By contrast, a preferred tactile sensing node may contain one or more of surface roughness, contact force measurement, thermal conductivity, hardness, temperature, and/or proximity sensors. Such additional modalities preferably allow a preferred tactile sensor node to characterize an object in a more comprehensive fashion.

Another exemplary multi-modal sensor node that may be formed on a surface of the sensor chip is a flow sensor node. A preferred multi-modal flow sensor node can characterize a boundary-layer flow field in a comprehensive fashion, with high spatial and temporal resolution. Such exemplary multi-modal flow sensor nodes may be used, for example, in real-time monitoring of a flow field in underwater vehicles and structures, and in characterizing flow fields around models in experimental wind or water tunnels.

Traditional flow sensors are based on hot-wire anemometry for measuring flow speed, or diaphragms for measuring pressure distribution. Such different sensors typically have been based on specific structures that are significantly incompatible with fabrication processes and materials. Accordingly, it has been impossible to measure several flow parameters locally and with a distributed array. By contrast, a preferred multi-modal flow sensor node includes one or more of various flow sensors, including, for example, surface micromachined artificial haircell sensors (for flow rate), surface micromachined hot-wire anemometers (for flow speed distribution, preferably along three axes), and surface micromachined diaphragms, preferably manufactured from Parylene, for pressure sensors and shear stress sensors (for vortex and drag detection).

A preferred sensor chip substrate is manufactured primarily from polymer-based materials, as opposed to silicon. Because silicon is a relatively fragile material for sensors, sensor chips made out of polymer material offer desirable mechanical flexibility and robustness compared with silicon counterparts. However, most existing polymer materials such as silicone elastomer, polyimide, and plastics cannot host signal processing electronics like silicon substrates do.

Hence, a preferred sensor chip integrates flexible polymer devices with discrete silicon chips for signal processing. The silicon chips (islands) are selected and designed so as not to significantly impede the overall mechanical flexibility and surface integrity of the sensor chip, and so that they can be integrated in efficient manufacturing processes without significantly compromising cost.

Exemplary applications of a preferred sensor chip include, but are not limited to, smart tactile skins for sensor-rich surgical tools, robotics manipulators, computer periphery input devices, and smart toys having sensor input. Preferred sensor chips having flow sensors may be useful for, e.g., smart flow sensing skins for underwater robots (e.g., for exploration or mine detection), underwater vehicles and infrastructures (e.g., oil drilling stations in deep sea), and scientific exploration and measurement (e.g., wind tunnels). Preferred embodiments of the sensory chip have the potential to make a significant impact on a broad range of applications for industry, exploration, military, and security, as nonlimiting examples.

Referring now to FIG. 1, an exemplary sensor chip 10 is shown, embodied in a flexible polymer-based substrate 12 forming a skin, and including a plurality of multi-modal sensor nodes 14, shown as multi-modal tactile sensor nodes. As shown in FIG. 1, the multi-modal sensor nodes 14 are repeated over an n×n array (as shown, 3×3) to form the sensor chip 10. A preferred multimodal tactile sensor node, for example, includes multiple sensor modalities (hardness, thermal conductivity, temperature, contact force, surface roughness). These nodes 14 in an exemplary embodiment are repeated with a spatial frequency of approximately 1 per 1 $cm^2$, though this repetition or particular distribution is not necessary. For example, individual nodes may have the same number of sensors or a significantly different number and/or type of sensor. Also, the spatial frequency of the nodes can vary, and may be greater or fewer than 1 per 1 $cm^2$.

The multi-modal sensor node 14, a tactile sensor node, includes a temperature sensor 16, a thermal conductivity (thermal flux) sensor 18, and a contact force and measured hardness sensor 20. The multi-modal sensor node 14 also includes a reference hardness sensor 22 for use with the contact force and measured hardness sensor 20. Sensors may also be implemented for such tasks as object identification and impending slippage detection. In the preferred tactile sensor node 14, a reference nickel resistance temperature device (RTD) of the temperature sensor 16 provides temperature measurement and compensation, a gold heater 24 and nickel RTD 26 pair provides thermal conductivity measurement for the thermal conductivity sensor 18, and the membrane NiCr (nichrome) strain-gauge based contact force and hardness sensor 20 with the reference contact hardness sensor 22 measures hardness.

The substrate 12 is preferably made of a polymer-based material. In an exemplary sensor chip 10, the substrate is a 2 mil thick Kapton HN200 polyimide film, manufactured by E.I. DuPont de Nemours and Co. The polymer substrate allows flexibility, robustness, and low material cost. Flex channels 30 are provided in the substrate along two dimensions by forming indentations in the substrate 12. The flex channels 30 provide enhanced and controlled flexibility to the substrate 12.

Figure 2:
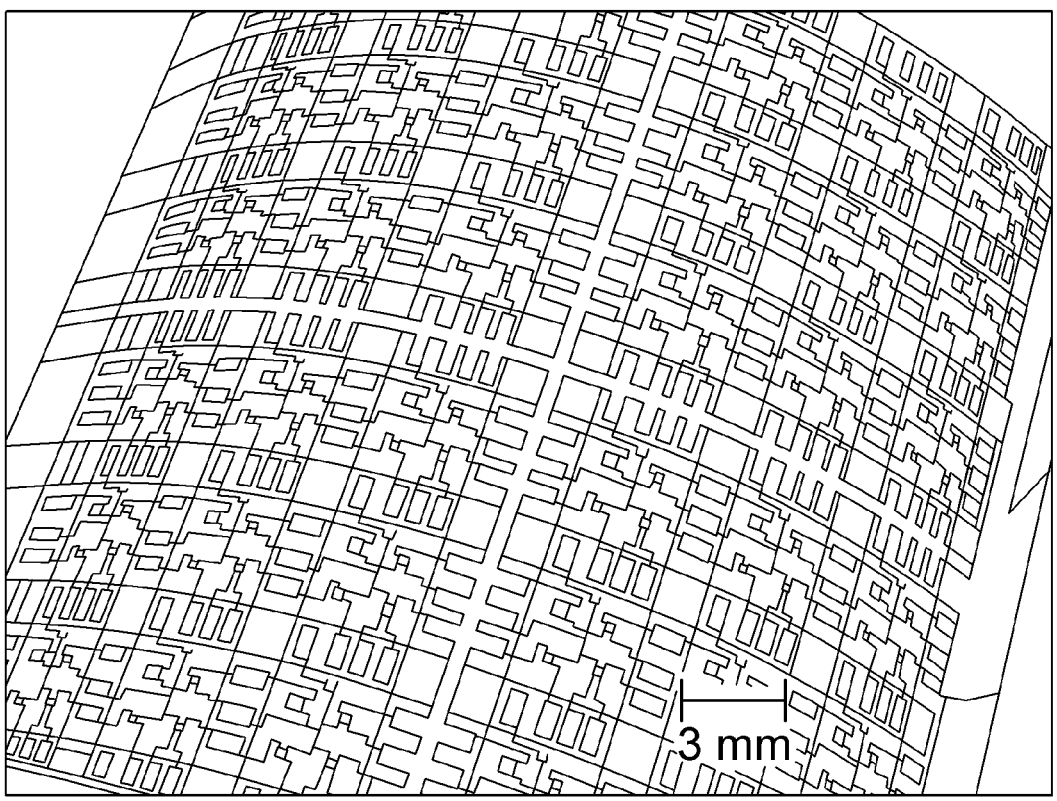
FIG. 2 shows a flexed sensor chip, according to a preferred embodiment of the present invention.

In addition, the contour of the substrate 12 is sensed in an integrated fashion using mapping sensors 32 embodied in microscale strain gauges, also preferably made of NiCr, and dispersed between the sensory nodes 14 (as shown in FIG. 1, the tactile sensor node). The mapping sensors 32 are dispersed between the sensory nodes 14 to sense bending of the substrate. In this way, the contour of a bent skin is sensed in an integrated fashion using the mapping sensors 32. For example, when the sensor chip 10 is mounted on a curved or compliant surface (e.g., a robotic finger tip), as shown by example in FIG. 2, the spatial relation of the multi-modal sensor nodes 14 is mapped to coordinate manipulation in three-dimensional space.

Individual sensing elements will now be described in more detail. As shown in FIG. 1, a preferred temperature sensor 16, for example, includes a nickel resistance temperature device (RTD) 34 that is used to measure the temperature of the operating environment as well as contact objects. This information is important for temperature compensation of the measurements of the other sensors as well as providing contact object information. The temperature sensor 16 and other sensor components are connected to other parts of the sensor chip, such as a processor, by leads 36.

Because all the sensors 16, 18, 20, 22 incorporated on the exemplary tactile sensing node are based on thin film metal resistors, all of them will function as RTDs to one extent or another based on the TCR (thermal coefficient of resistance) of the base material. This value is low for NiCr, making it a good choice for rejecting thermal disturbances, but is high for nickel and gold. Gold is not used for a preferred RTD due to its low resistivity. By using nickel, a high TCR is provided with the added benefit of increased resistivity to decrease the effect of parasitic resistances. The TCR of each sensor is characterized to allow temperature compensation by calibrating the reference nickel RTD, for example, by heating the sensor chip 10 and observing the changes in resistance with temperature, then calculating the base metal TCR.

Hardness of a contact object is an important parameter for object identification and manipulation. This measurement modality is lacking in most conventional tactile sensors. Existing micromachined hardness sensors require that the applied force be known, use a known calibrated integral actuator force, or use changing resonant frequency under ultrasonic vibration. The required assumptions, complexity, and size limitations of such approaches do not lend themselves to a distributed multi-modal sensor chip. By contrast, a preferred hardness sensor 40 shown in FIGS. 3A-3B is a passive hardness sensor that does not rely on actuation or knowledge of contact force.

Figure 3A:
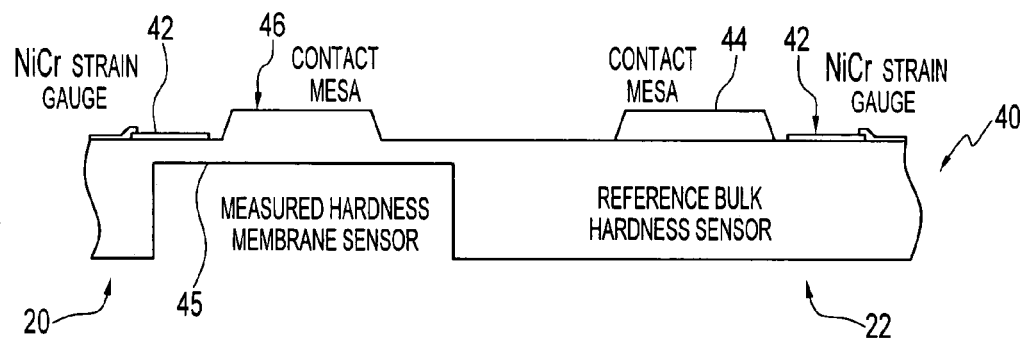
FIGS. 3A and 3B show a cross section of a hardness sensor, and the hardness sensor in contact with an object, respectively, according to a preferred embodiment of the present invention.
Figure 3B:
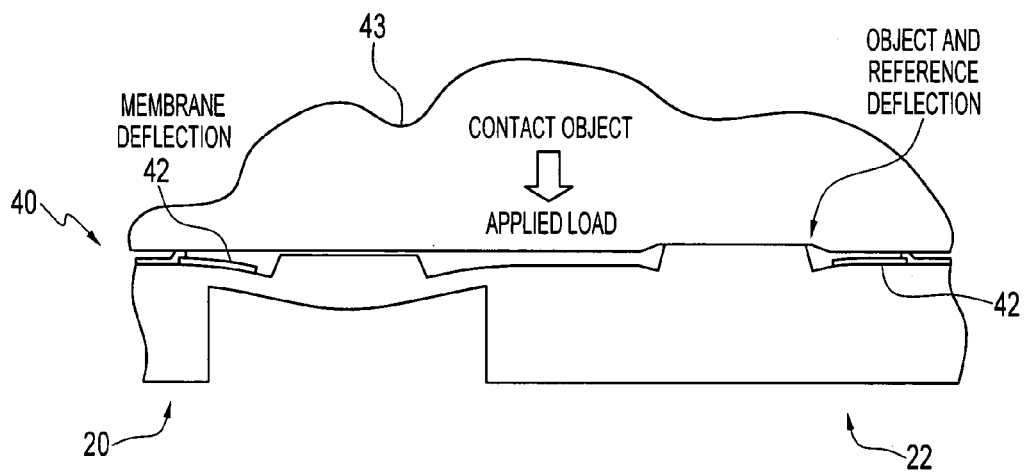

Referring now to FIGS. 3A-3B, the passive hardness sensor 40, which may be incorporated into the multi-modal sensory node 14, derives a hardness of a contact object using two contact sensors of different support stiffness: the contact force and measured hardness sensor 20 and the reference hardness sensor 22. The preferred hardness sensor does not rely on knowledge of contact force. In a preferred embodiment, the measurement sensor 20 is mounted on a polymer membrane, while the reference sensor 22 is built on the bulk substrate 12. Both the measurement sensor 20 and the reference sensor 22 include a strain gauge 42, which may be made from NiCr, for example, to measure response. A differential response between the measurement sensor 20 and the reference sensor 22 is used to measure the hardness of a contact object 43.

The structure of the preferred hardness sensor 40 within the sensor node 14 is shown in FIG. 3A and in cross section in FIG. 3B. The exemplary hardness sensor 40 includes the measurement sensor 20 on a square polymer diaphragm 45 and a reference sensor 22 on the bulk polymer substrate 12.

Both sensors 20, 22 include a contact mesa 46 with the strain gauges 42 situated on the periphery of these mesas. The square of a diaphragm 45 of the measurement sensor 20 has a relatively low stiffness and for a given maximum central displacement requires a uniform pressure according to clamped-clamped plate theory as shown in Eq. 1.

$$q_{plate} = \frac{z_{max}Et^3}{(0.0138)b^4} \quad (1)$$

In Eq. 1, $z_{max}$ is the peak vertical deflection in the center of the diaphragm 45, $q_{plate}$ is the pressure applied to the plate, b is the length of the square sides, E is the material modulus, and t is the plate thickness.

The preferred reference sensor 22 does not use a diaphragm; rather the contact mesa 44 and the strain gauges 42 are positioned over full thickness bulk polymer 12. The stiffness of the bulk reference sensor 22 is thus much higher than the measurement sensor diaphragm 45. The preferred reference sensor 22 requires a uniform pressure for a given deflection according to Eq. 2.

$$q_{bulk} = \frac{z_{max}E}{(2.24)a(1-v^2)} \quad (2)$$

In Eq. 2, v is the bulk material Poisson's ratio, a is the contact mesa 46 width, and $q_{bulk}$ is the pressure applied to the bulk sensor contact mesa. This model assumes that the reference sensor 22 behaves like a semi-infinite block under a uniform pressure over the area of the contact mesa.

When the sensor chip 10 is in contact with the object 43, changes in resistance are observed at both the measurement and reference sensor strain gauges 42. The measured resistance changes are converted to a peak deflection ($z_{max}$) with calibrated resistance versus displacement data and used to find the apparent pressures $q_{plate}$ and $q_{bulk}$ with Eqs. 1 and 2. The contact object hardness 43 is related to the ratio of apparent pressures.

Measurement of contact forces can also be performed using the measurement sensor 20 and the reference sensor 22. Based on the known geometry of the devices, the pressures can be equated to normal force. The differential stiffness of the two sensors 20, 22 allows two different ranges of contact forces to be measured.

In an experimental operation of the hardness sensor 40, a number of polymer samples were placed in contact with the sensor skin 12. A range of reference samples of sorbothane and polyurethane rubber with known hardnesses ranging from 10 to 80 Shore A were cut into 5 mm by 5 mm squares and pressed onto the sensor skin 12 using a fixed mass (147 g). The change in resistance of each sensor 20, 22 was converted to an equivalent displacement using calibration data. Calibration data was generated by measuring the change in resistance of the measurement membrane sensor 20 and the bulk reference sensor 22 in response to a known normal displacement provided by a micromanipulator probe coupled to a precision linearly variable differential transformer (LVDT).

Figure 4:
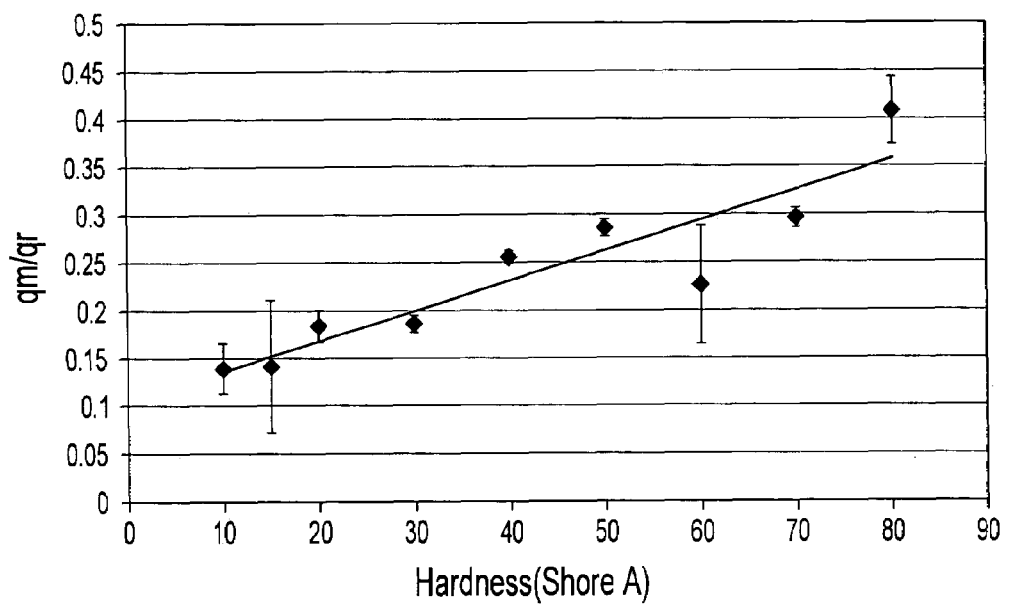
FIG. 4 shows a differential response between the membrane hardness sensor and a reference sensor versus object hardness, with a linear fit line.

The proportionality between pressure ratio and object hardness is shown in the graph of FIG. 4. A large amount of scatter was observed in the hardness data as can be seen in the graph. This is attributable to the surface roughness of the rubber samples. Nevertheless, a clear overall trend is observed when a large number of data points are averaged as in FIG. 4, showing an increase in pressure ratio with object hardness.

The thermal conductivity of the contact object 43 is another important piece of data for object identification. The thermal conductivity sensor 18 operates by observing the changing resistance of the nickel RTD 26 in response to an input to the gold heater 24. The thermal conductivity of the contacting object 43 is a useful measure for object discrimination, and in concert with other sensing modes can expand the capabilities of the overall sensor chip 12 by helping to distinguish between equally "hard" objects for example.

Figure 5:
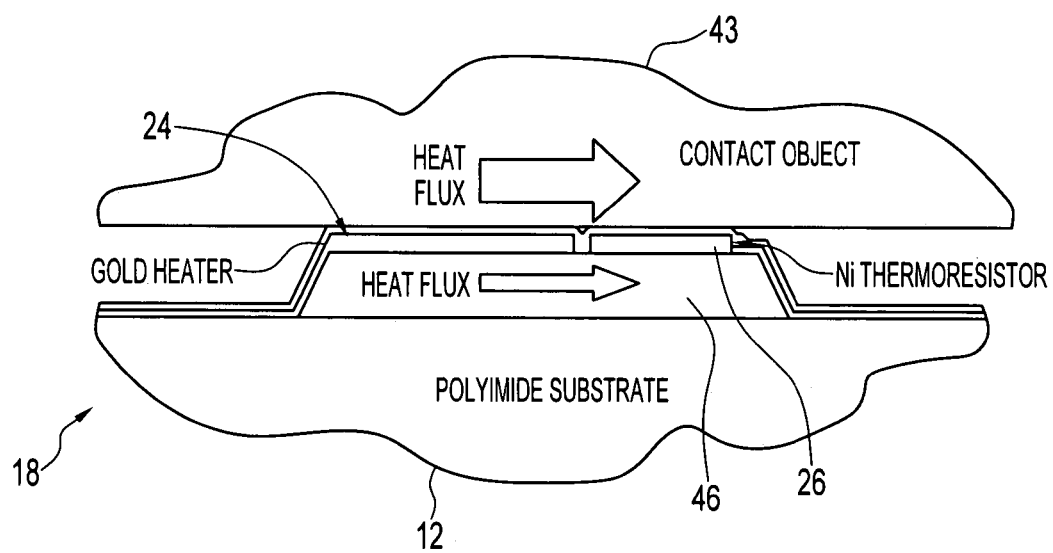
FIG. 5 shows a preferred embodiment of a thermal conductivity sensor, according to an embodiment of the present invention.

As shown, the value is derived by measuring heat flux between the heater 24 and the temperature sensor 26, which are disposed on the polyimide substrate 12. The heater 24, preferably manufactured from gold as described above, is disposed on a bump 48 (FIG. 5) formed on the substrate 12, and is situated near, yet separated from, the temperature sensor 26. The exemplary temperature sensor 26 is embodied in an Ni RTD thermoresistor, also disposed on the bump 48. The heat transfer between the heater 24 and the temperature sensor 26 is altered when the contact object 43 contacts the surface of the sensor chip 12 over the thermal conductivity sensor 18, which changes the thermal transfer path. The heat flux travels through the contact object 43 as well as the substrate 12, which changes the signal measured at the temperature sensor 26. A stepped power input to the heater generates a signal at the temperature sensor with a time constant that varies with the thermal conductivity of the contact object.

When not in contact with the object 43, the only route for the heat input of the heater 24 to reach the RTD of the temperature sensor 26 is through the polyimide substrate 12 and the surrounding air. When the object 43 comes in contact with the thermal conductivity sensor 18, the low efficiency heat path through the air is replaced by solid conduction, changing the character of the signal measured at the temperature sensor 26. Using an Ni RTD as the temperature sensor 26, for example, with a square wave voltage input to the heater, the temperature of the temperature sensor can be modeled as a simple first order system according to Eq. 3.

$$T_{RTD}(t) = 1 - e^{-t/\tau} \quad (3)$$

Where T is the time constant of the first order system, giving a measure of how quickly the system responds to an input. The time constant of the temperature of the temperature sensor 26 is found to be a function of contact object thermal conductivity. This method was found to correlate well to contact object thermal conductivity.

In an exemplary operation, characterization of the performance of the thermal conductivity sensor is performed at room temperature (~22° C.) by inputting a 0-2VDC square wave at 0.3 Hz to the gold heater 24 and measuring the resulting change in resistance of the nearby Ni RTD 26. The resistance of the RTD is sampled at 10 Hz using an Agilent 33410A multi-meter and GPIB interface.

Figure 6:
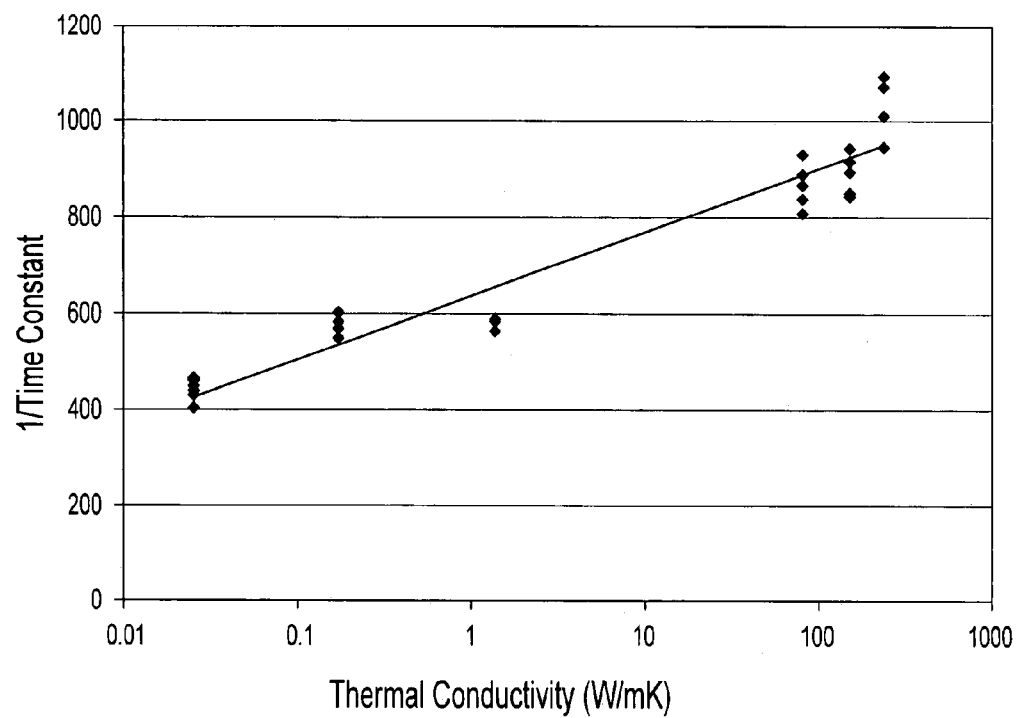
FIG. 6 shows a relationship between thermal conductivity and a time constant, in which step power input to a gold heater of a thermal conductivity sensor generates a signal at a nickel temperature sensor, with a time constant that varies with contact object thermal conductivity.

The thermal conductivity sensor 18 preferably should behave as a first order system with a time constant related to the object thermal conductivity. FIG. 6 shows the result of testing, where contact objects of various thermal conductivities (nylon 6, soda-lime glass, single crystal silicon, 300-series stainless steel, aluminum, and ambient air) were placed in contact with the surface of the thermal conductivity sensor 18, and the time constant of the resulting signal at the temperature sensor 26 was obtained through curve fitting. It was observed that the time constant decreases and the step response of the temperature of the temperature sensor 26 is faster with increasing thermal conductivity. Scatter is observed and expected due to changes in contact configuration from test to test due to surface roughness. The relationship between object thermal conductivity and time constant is found to be approximately logarithmic based on a curve fit of FIG. 6. As shown, more conductive objects result in faster response and smaller time constant.

Another type of sensing measures curvature of the substrate using the mapping sensor 32 described above. The mapping sensor 32 preferably embodied in integrated NiCr strain gauges dispersed between the sensor nodes 14 measures the x- and y-direction curvature of the flexible substrate 12. The mapping sensors 32 are positioned over the flex channels (trenches) 30 etched in the back of the polyimide substrate 12 to allow the substrate to preferentially bend in these regions. Processing of these measurements into bending angles using calibrated data allows a three-dimensional mapping of skin curvature state. The skin mapping sensors 32 are found to perform linearly ($R^2=0.996$) with respect to curvature with sensitivity of 44.25 ppm.

Figure 7:
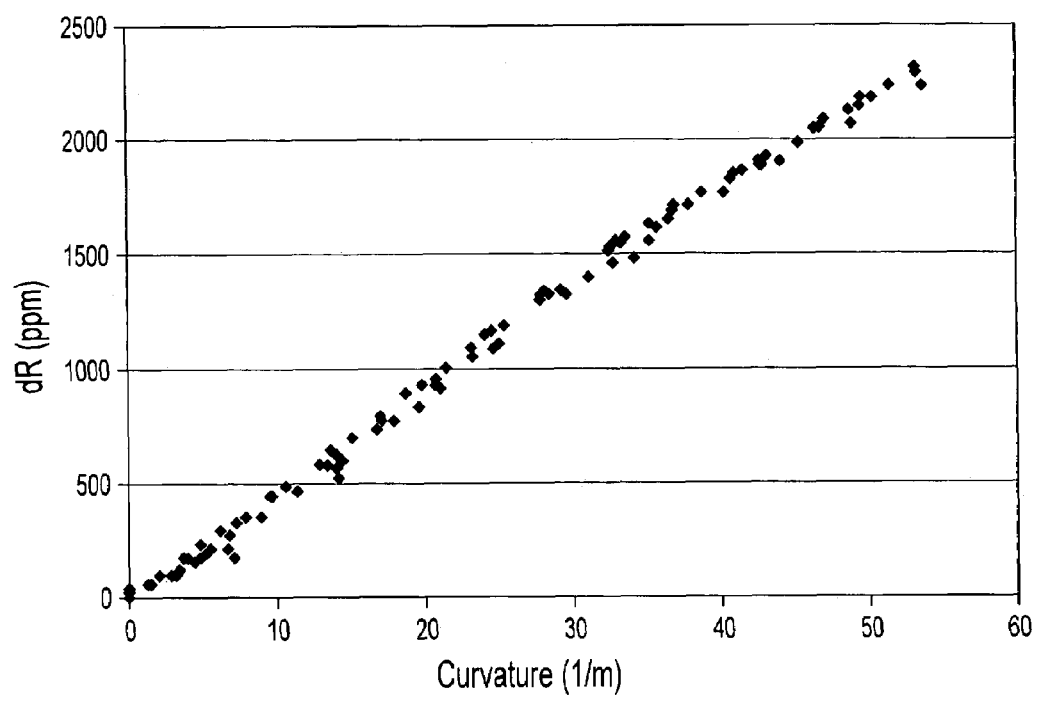
FIG. 7 shows a response of a skin mapping sensor to skin curvature, according to an embodiment of the present invention.

Skin curvature calibration is accomplished by flexing the substrate 12 under known displacement using a micromanipulator coupled to a precision linearly variable differential transformer (LVDT). Measurements are taken while bending and relaxing to assess visco-elastic hysteresis and plastic deformation. A resulting response of the; mapping sensors 32 versus skin flex for a number of tests is seen in FIG. 7.

The processing steps preferably do not have to involve high temperature steps or bulk micromachining, therefore they can be substrate neutral. Specifically, the microfabrication process can be carried out directly on flexible and low cost polymer substrates.

A description of an exemplary fabrication process follows for the sensory chip and the tactile sensory node, referring to FIGS. 8A-8E. A polyimide film substrate 60, for example a 50 mm square sheet cut from a sheet of DuPont Kapton HN200 polyimide film is provided. This film 60 is preferably about 50 μm thick, though other thicknesses may be used. During the fabrication of the polyimide film 60, one surface of the film is in contact with a roller and the other is untouched. In practice, measurements with an optical vertical scanning interferometer (VEECO LM1000) showed very small roughness differences between the free and roller faces (197 nm and 243 nm Rq respectively). Prior to photolithography, the polyimide film substrate 60 is cleaned and then baked at 350° C. under nitrogen at 1 Torr for 2 h.

Figure 8A:
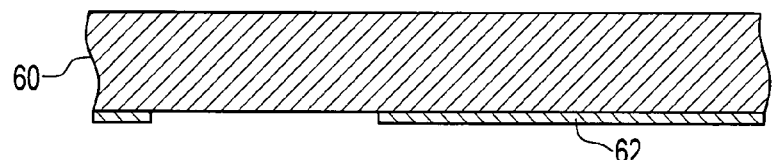
FIGS. 8A-8E show an exemplary process for manufacturing a sensor chip having sensors, according to a preferred embodiment of the present invention.
Figure 8B:
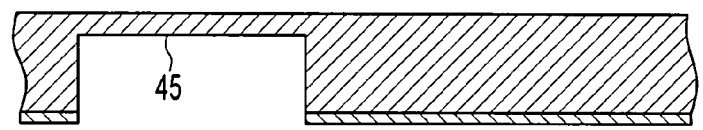

Once the polyimide film substrate 60 has been cured, an aluminum etch mask 62 is deposited and patterned via lift off on the "rough" roller side of the film (FIG. 8A). The film substrate 60 is then etched in an oxygen plasma reactive ion etcher at 350 W with 300 mT oxygen pressure (FIG. 8B) to define the flex channels 30 and the membrane sensor diaphragms 45. The film 60 preferably is etched 40 μm down at a rate of ~330 nm per minute. This plasma-etching step preferably is performed first to avoid erosion of backside metal layers that may otherwise occur.

Figure 8C:
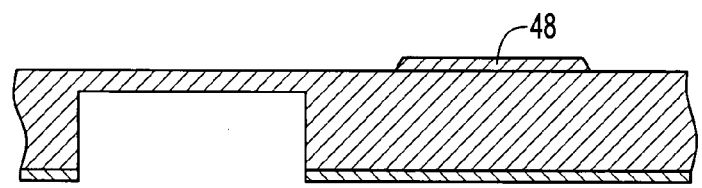
Figure 8D:
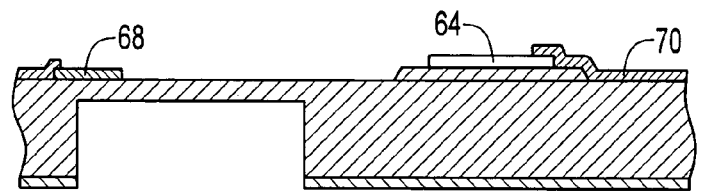
Figure 9A:
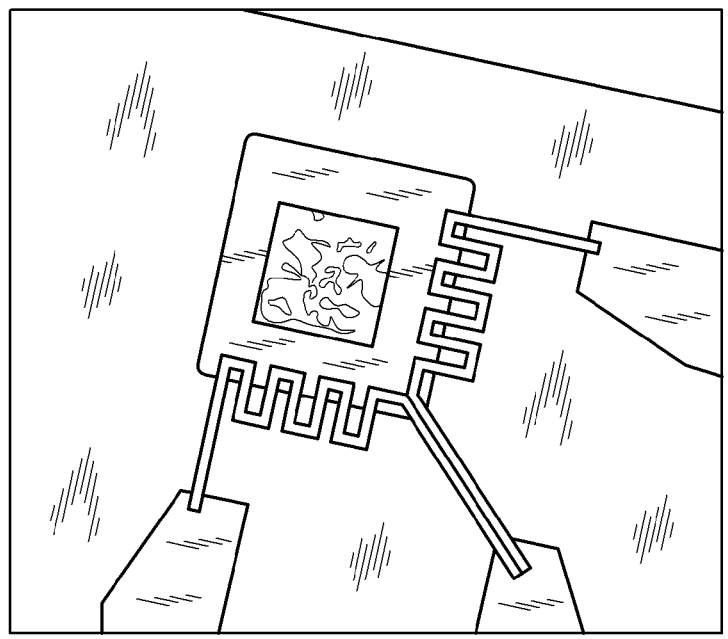
FIG. 9 shows a membrane hardness sensor with a nichrome string gauge, and a reference bulk sensor, respectively.
Figure 9B:
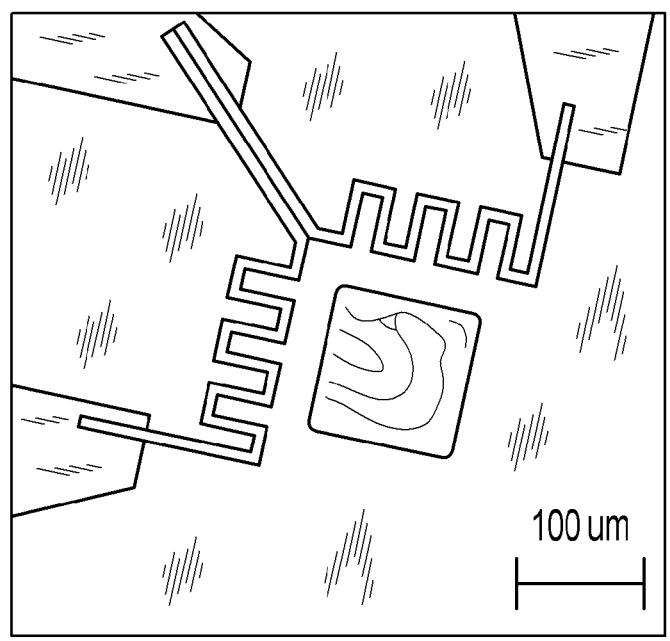

With the sensor node 14 regions and contact force membranes defined, a 2-μm-thick layer of photo-definable polyimide (for example, HD Microsystems HD4000) is spun on the smoother top skin surface and patterned to define contact mesas 46 for the thermal conductivity 18 and reference RTD sensors 22 (FIG. 8C). FIGS. 9A-9B show exemplary RTD strain gauges on a membrane hardness sensor 20 and a reference bulk sensor 20, respectively. This layer is aligned to the backside features via alignment marks visible due to the optical clarity of the HN200 film. Once patterned, the polyimide layer is cured under 1 Torr of nitrogen at 350° C. for 2 hours.

Next, nickel RTDs 26 are patterned and deposited on the contact mesas 46. For example, nickel (e.g., 500 Å Ni) 64 is thermally evaporated via e-beam on top of a 100 Å chrome adhesion layer (not shown). Then, 750 Å of NiCr 68 is deposited and lifted off to define the strain gauges for the force 20, curvature (mapping) 32, and hardness sensors 22. Preferably, no adhesion layer is used. In order to achieve the relatively high resolution required for the minimum NiCr (10 μm) and Ni (15 μm) feature widths on a flexible polymer substrate, in a preferred embodiment, the Kapton film 12 is temporarily attached to a Pyrex substrate via surface tension by wetting the substrate with a drop of deionized water. The RTDs 26 are patterned preferably via liftoff using standard image reversal photolithography. The last metal layer comprises 1500 Å of gold 70 on a 100 Å chrome adhesion layer that is thermally evaporated and lifted off (FIG. 8D), forming wiring 36. Before each metal deposition step 60, the film substrate is placed in oxygen planar plasma for 3 minutes at 300 W to remove photoresist residue from image reversal and to improve metal adhesion to the polymer film.

Figure 8E:
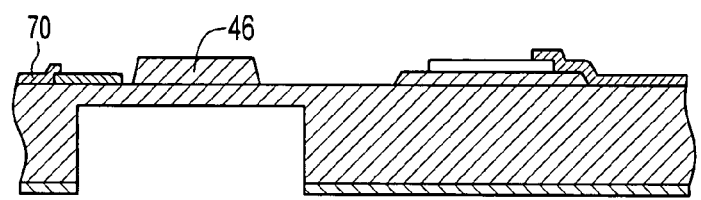

The final step is to spin on and pattern the tactile contact bumps 46 for the force and hardness sensors (FIG. 8E). The bumps 46 are defined from an 8-μm-thick layer of HD4000 photo-definable polyimide in the center of each sensor. The polyimide is cured for 2 hours at 350° C. and 1 Torr nitrogen.

Another embodiment of the present invention includes a sensor node for flow sensing. The substrate may be polymer-based as in the substrate supporting the tactile sensor node 14.

Comprehensive flow sensing in the fluid boundary layer involves measurement of, for example, pressure, shear stress (drag and vortex), temperature, and three-axis flow rates. The spatial and temporal evolution of surface flow features is extremely difficult to obtain due to limitations of scientific instruments.

Conventional flow sensing instruments such as hot-wire anemometers are singular point measurement devices only. They suffer from a number of bottlenecks: their sizes are large and may change the characteristics of the flow; it is extremely difficult to measure multiple flow parameters including vector speed, pressure, and shear stress, which is proportional to the gradient of velocity in the boundary layer; and it is difficult to characterize a flow field within a thin boundary layer (thickness on the order of 1 mm).

Microfabricated flow sensing surfaces with multiple sensing modalities to record pressure, shear stress, and flow rates would be useful for experimental fluid mechanical studies and for underwater vehicles and platforms. Such sensors preferably would be fabricated using efficient, low cost techniques. They preferably would allow integration of microelectronics signal processing units, and should be relatively mechanically robust.

Potential application scenarios for multi-modal flow sensors may include, but are not limited to: comprehensive monitoring of liquid flow field for underwater vehicles and structures, such as autonomous underwater vehicles, deep-sea drilling stations, and military vehicles for possible drag reduction; and comprehensive monitoring of air flow conditions for aircrafts and unmanned vehicles.

A large sensitive skin could be used to cover an object with a large area and curved surfaces. For example, an aerodynamic model used in an experimental wind- or water-tunnel may be covered with the sensitive skin in strategic regions to provide direct experimental characterization of flow field. Such flow field data has been prohibitively difficult to obtain in the past. Such comprehensive results can be used to validate and improve theoretical models or provide aerodynamic design insights.

Figure 10:
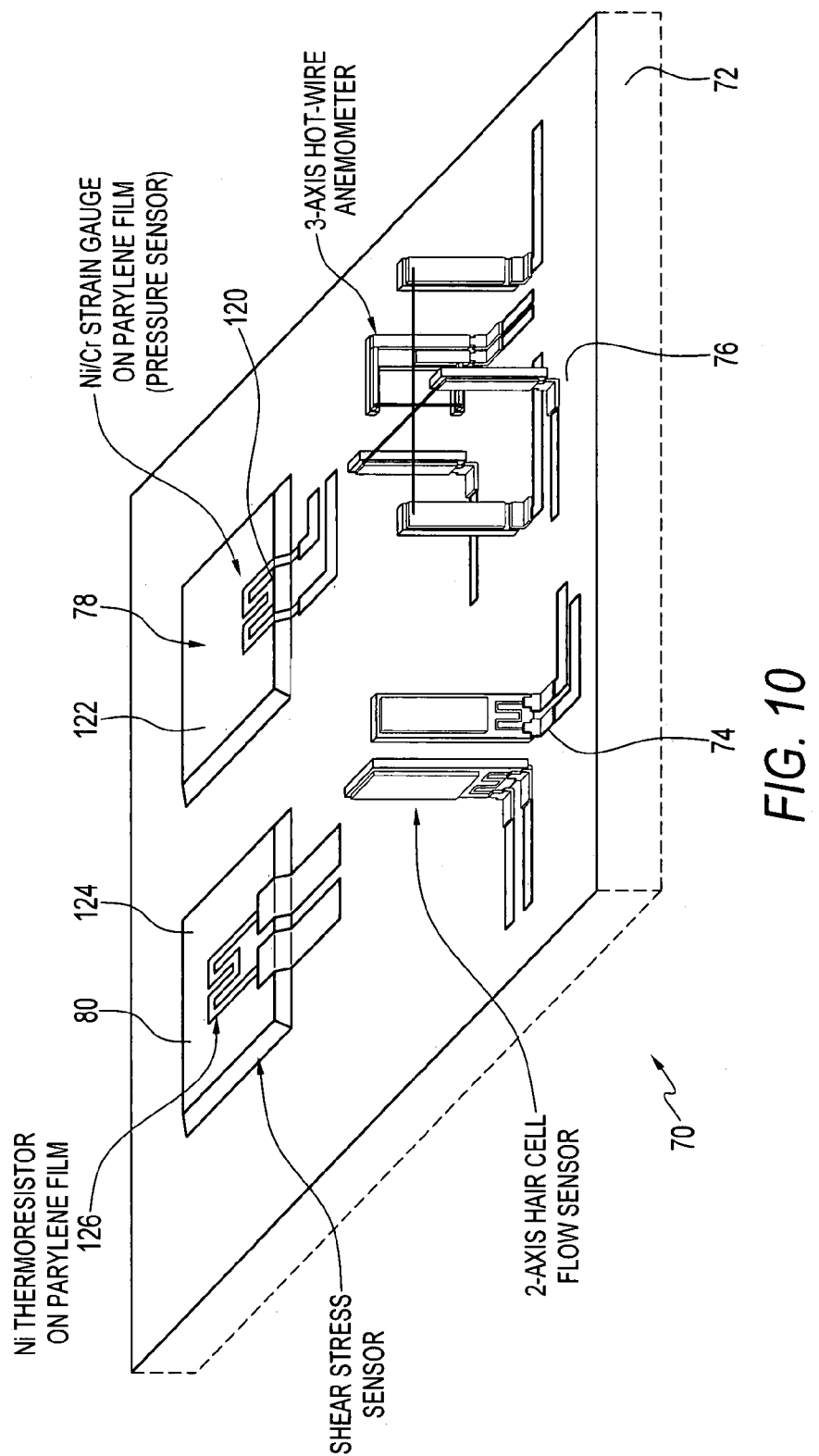
FIG. 10 shows an exemplary flow sensory node, according to another embodiment of the present invention.

The diagram of an exemplary single sensor node is illustrated in FIG. 10. According to an embodiment of the present invention, the node 70, which may be disposed on a flexible, polymer-based substrate 72, is provided with one or more of the following sensing units: an artificial haircell 74 for measuring three-dimensional flow velocity, one or more hot-wire anemometers 76 along one or more dimensions for measuring the velocity of flow at different distance to the boundary layer, a pressure sensor 78 for monitoring pressure variation, and a shear stress sensor 80 for measuring surface vortex. Various sensors may be integrated together on the polymer substrate using novel material and fabrication processes as described herein.

Fish and many underwater animals utilize multimodal sensitive skin that can detect flow, pressure distribution, electrical potential and field, and local vortex. The lateral line is a primary sensing organ for fish. It usually spans the length of the fish body. Its main functions include (1) detection of water flow around the fish body, allowing a fish to maintain stability within turbulent currents and (2) detection of distant objects such as obstacles, prey and predators using direct or reflected waves. Linearly distributed along the lateral line are clustered haircell bundles embedded in a gel-like dome called a neuromast. Water flowing past the neuromasts imparts forces to the haircells and causes them to bend, with the extent of the bending determined by the speed of the flow. In certain species, the haircells lie outside of the epidermis; in others, they are embedded in sub-dermal canals for added protection against wearing and damages.

Figure 11A:
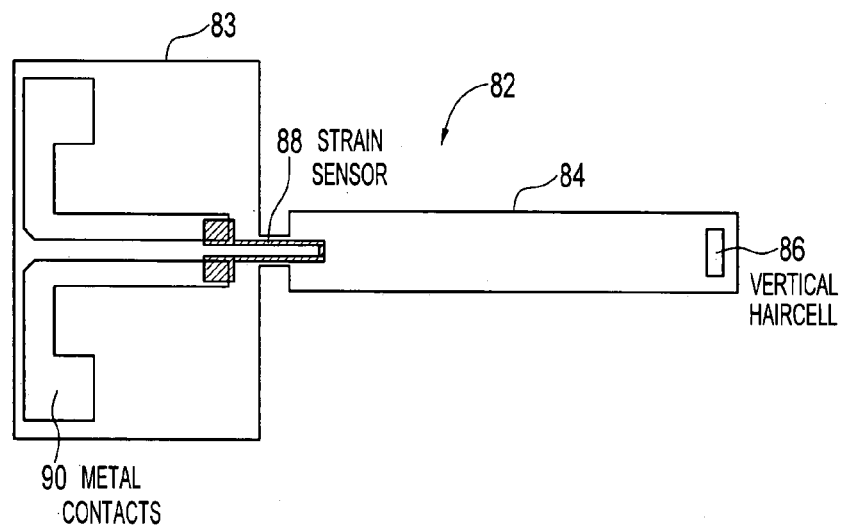
FIG. 11 shows a silicon based artificial haircell, according to an embodiment of the present invention.
Figure 11B:
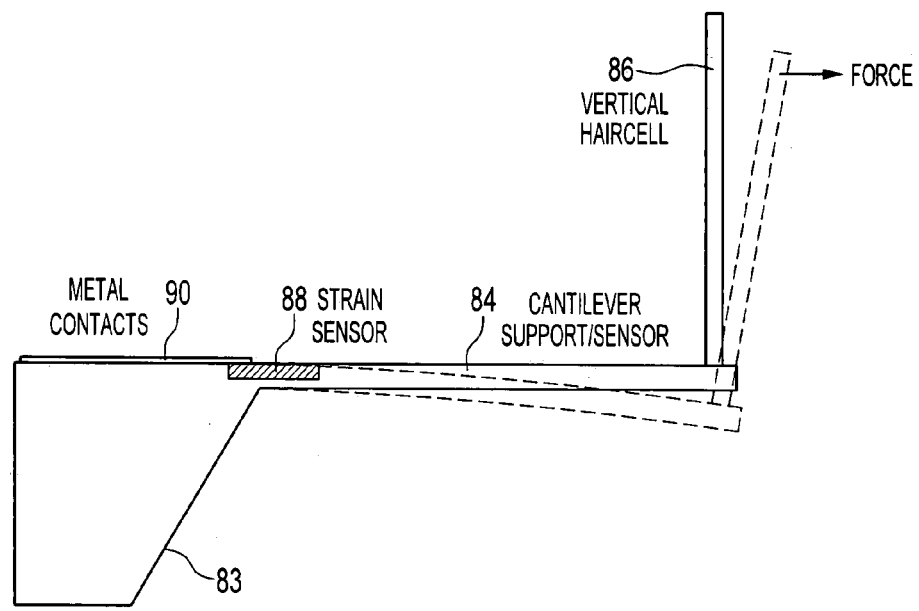

Artificial haircell sensors may be used for mimicking the lateral line system of fish. A schematic diagram of an exemplary haircell sensor 82, made of single crystal silicon substrate 83, is shown in FIG. 11. The haircell sensor 82 consists of an in-plane fixed-free cantilever 84 with a vertical artificial cilium 86 attached at the distal, free end. External flow parallel to the sensor substrate 83 impacts upon the vertical cilium 86. Due to rigid connection between the in-plane cantilever 84 and the vertical cilium 86, a mechanical bending moment is transferred to the horizontal cantilever beam, inducing strain at the base of the cantilever beam, which is detected using a strain sensor 88, such as a piezoelectric sensor producing a signal that is transmitted by conductive contacts 90. The magnitude of the induced strain can be sensed by many means, for example by using integrated piezoresistive sensors.

The vertical cilium 86 preferably is realized using a three-dimensional assembly technique called plastic deformation magnetic assembly (PDMA). A description of the PDMA process is provided in J. Zou, J. Chen, C. Liu, and J. Schutt-Aine, "Plastic Deformation Magnetic Assembly (PDMA) of Out-of-Plane Microstructures: Technology and Application; IEEE/ASME J. of Microelectromechanical Systems, Vol. 10, No. 2, pp. 302-309, June 2001, which is incorporated in its entirety by reference. A preferred assembly process allows reliable formation of three-dimensional structures in large array format. Multiple structures can be achieved at wafer-scale by a globally applied magnetic field. Position and height of the cilia can be controlled.

Figure 12:
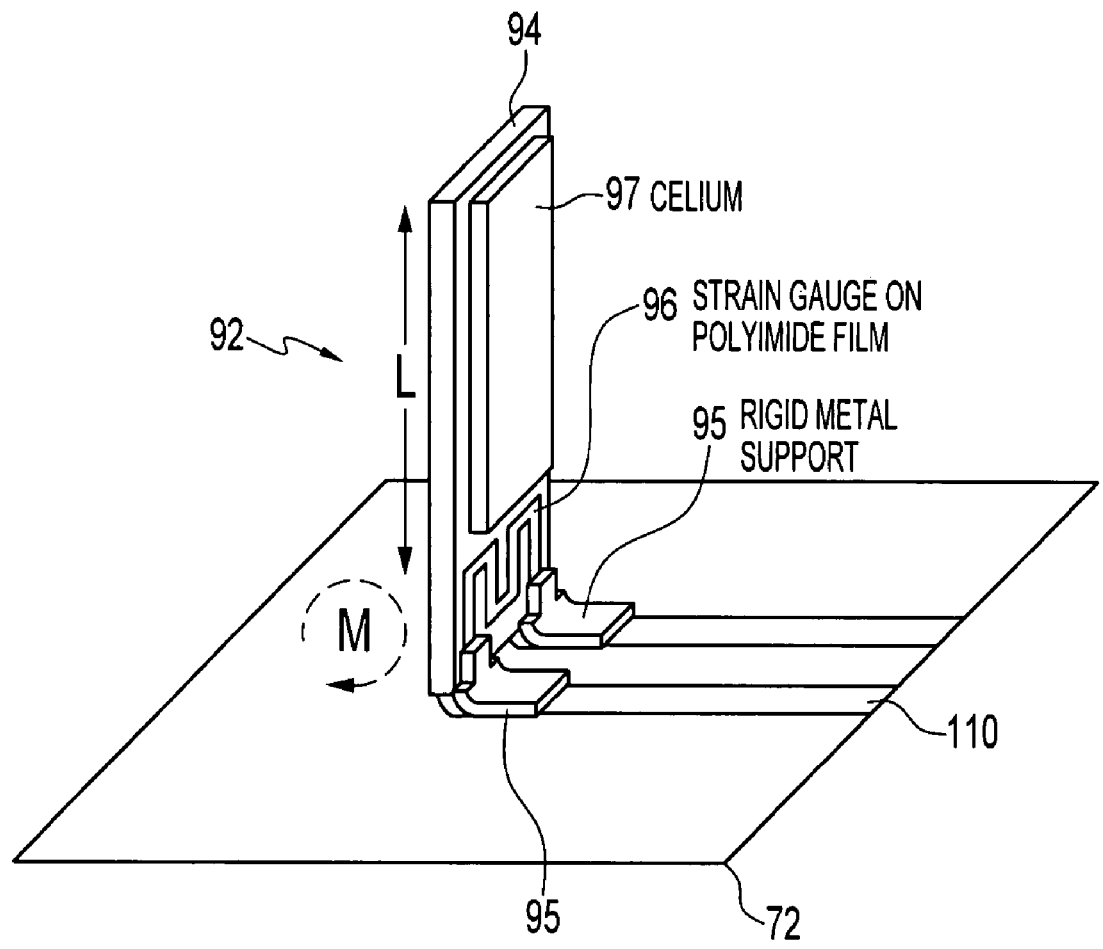
FIG. 12 shows a preferred artificial haircell (AHC), according to a preferred embodiment of the present invention.

A preferred polymer based haircell device is also provided, as shown by example in FIG. 12. An artificial haircell (AHC) 92 includes a vertical beam 94 (cilium) rigidly attached to the substrate 92. The vertical cilium 94 is made of surface micromachined polymer, and more preferably includes a stiff permalloy plating.

As shown in FIG. 12, the vertical cilium 94 is rigidly attached to the substrate 72 by one or more rigid metal supports 95. The substrate 72 can be any of various substrates, but preferably is a polymer-based substrate. Attached at the base of the vertical cilium 94, between the cilium and the substrate, is a strain gauge 96. The strain gauge 96 includes a thin film nichrome (NiCr) resistor on a thicker polyimide backing that runs the length of the cilium 94. The piezoresistive strain sensors 96 are located on the piece that is assembled (i.e., the vertical cilium 94) using three-dimensional assembly.

When an external force is applied to the vertical cilium 94, either through direct contact with another object (functioning as a tactile sensor) or by the drag force from fluid flow (flow sensing), the beam will deflect and cause the strain gauge 96 to stretch or compress. The strain gauge region is treated as being rigidly attached to the substrate 72, while the cilium 94 is free. The magnitude of the induced strain (e) is largest at the base, where the strain gauge is located, $$\varepsilon = \frac{M t_{PI}}{2EI} \tag{4}$$

where M is the moment experienced at the base, $t_{PI}$ is the polyimide thickness, and E and I are the modulus of elasticity of and the moment of inertia of the polyimide. The very thin nichrome resistor of the strain gauge 96 is not taken into account.

The vertical cilium preferably is surface micromachined and deflected out of plane using magnetic 3D assembly, such as PDMA, and can be conducted on a wafer scale. The vertical cilium 94 remains in deflected position due to plastic deformation at the joint.

Figure 13A:
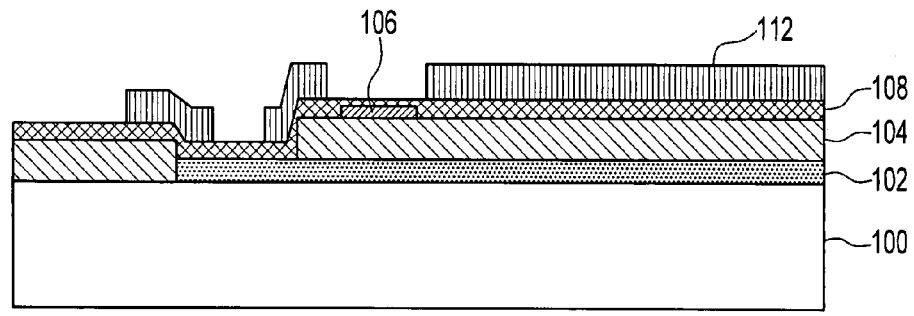
FIGS. 13A and 13B show steps in a preferred process for manufacturing the AHC of FIG. 12, according to a preferred embodiment of the present invention.

A preferred fabrication method includes a series of metallization and polymer deposition steps. Referring to FIG. 13A, first, on a substrate 100 a 0.5-μm Al sacrificial layer 102 is evaporated and patterned. Then, a 5.5-μm photodefinable polyimide 104 (e.g., HD-4000 from HD Microsystems) is spun-on and patterned photolithographically. The polyimide 104 is cured at 350° C. in a 1 Torr $N_2$ vacuum for 2 hours. Preferably, this is the highest temperature used in the process, allowing the AHC to be fabricated on various substrates 100, including polymer-based substrates.

Afterwards, a 750-Å-thick NiCr layer 106 used for the strain gauge 96 is deposited by electron beam evaporation. This is followed by a 0.5-μm-thick Au/Cr evaporation 108 used for electrical leads 110 and the bending hinge. The Au/Cr layer 108 is then used as a seed layer to electroplate approximately 5 μm of permalloy 112 before being removed by lift-off. The resulting structure is shown in FIG. 13A. The final surface micromachining step is another 2.7-μm polyimide film (not shown) to serve as a protective coating for the permalloy cilium and the NiCr strain gauge.

The Al sacrificial layer 102 is then etched in a TMAH solution for over a day to free the structure. The sample is then carefully rinsed and placed in an electroplating bath 113, where an external magnetic field is applied that interacts with the permalloy 112 to raise the vertical cilium 94 out of plane.

Figure 14:
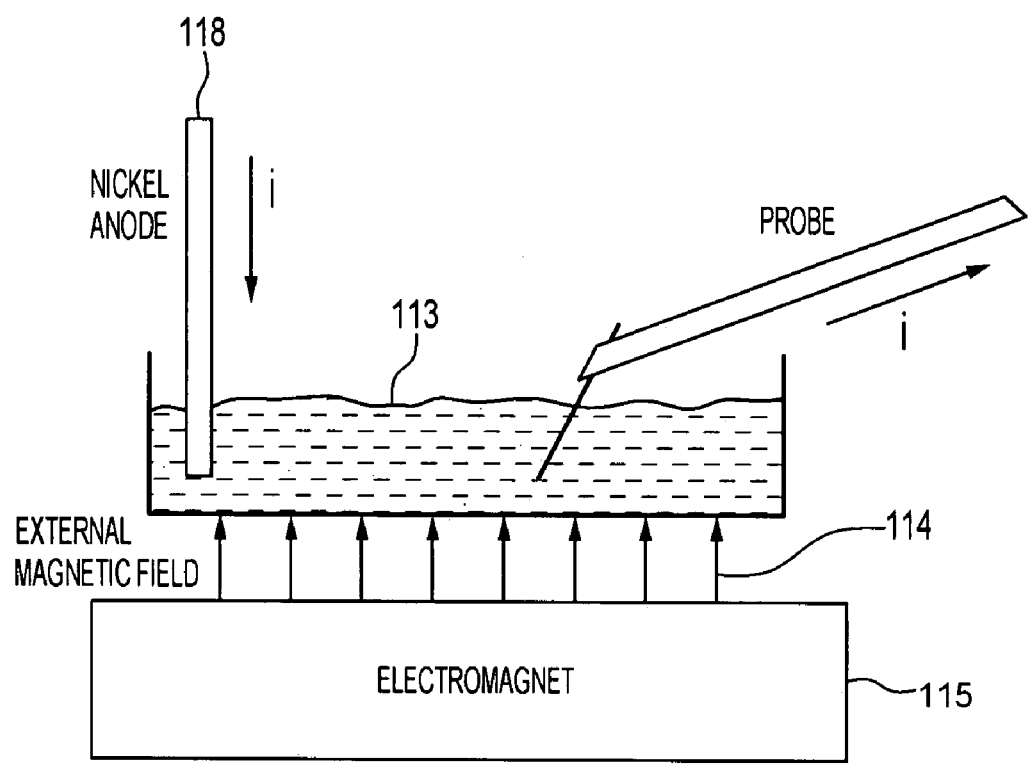
FIG. 14 illustrates a post release Ni plating set up, in which an external magnetic field is used to raise the AHC of FIG. 12, according to a preferred embodiment of the present invention.

For example, in a post-release Ni plating setup, shown by example in FIG. 14, an external magnetic field 114 is applied with an electromagnet 115 during the electroplating process. Preferably, the entire process is done under a microscope. After a few minutes of plating, the magnetic field 114 is removed and the cilium remains permanently out of plane.

Figure 13B:
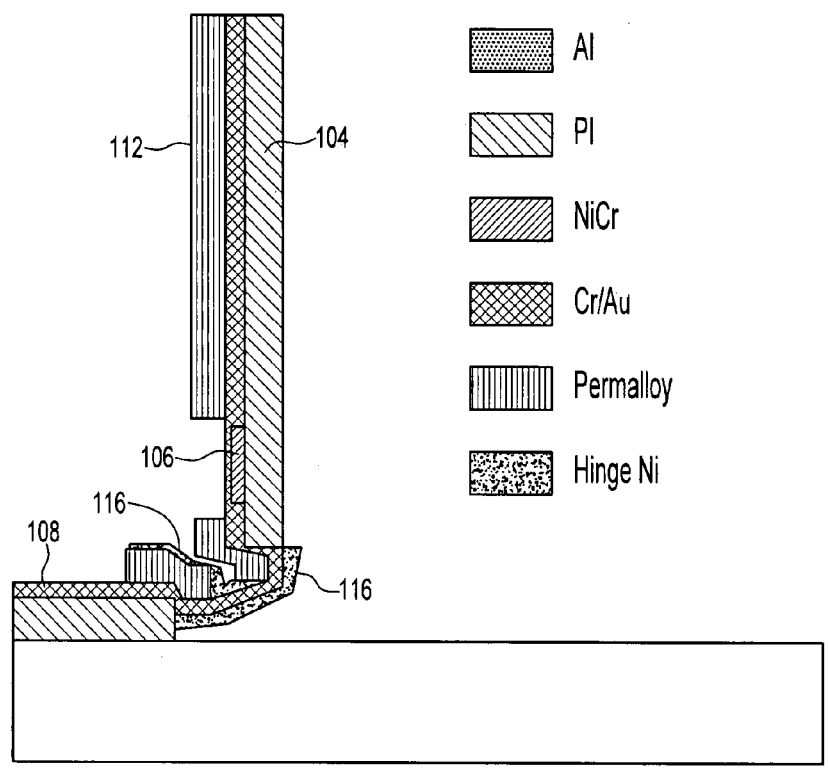

While the external field is being applied, Ni 116 is electroplated on the Au hinge using a nickel anode 118, which rigidly fixes the structure out-of-plane to the substrate and reinforces the ductile Au hinge, as shown in FIG. 13B. The Ni electroplating is done on the substrate globally, preferably lasting about 20 minutes to achieve a thickness of approximately 10 mm. The actual thickness is difficult to measure and control, but is not important as long as it is rigid relative to the polyimide film.

Figure 15A:
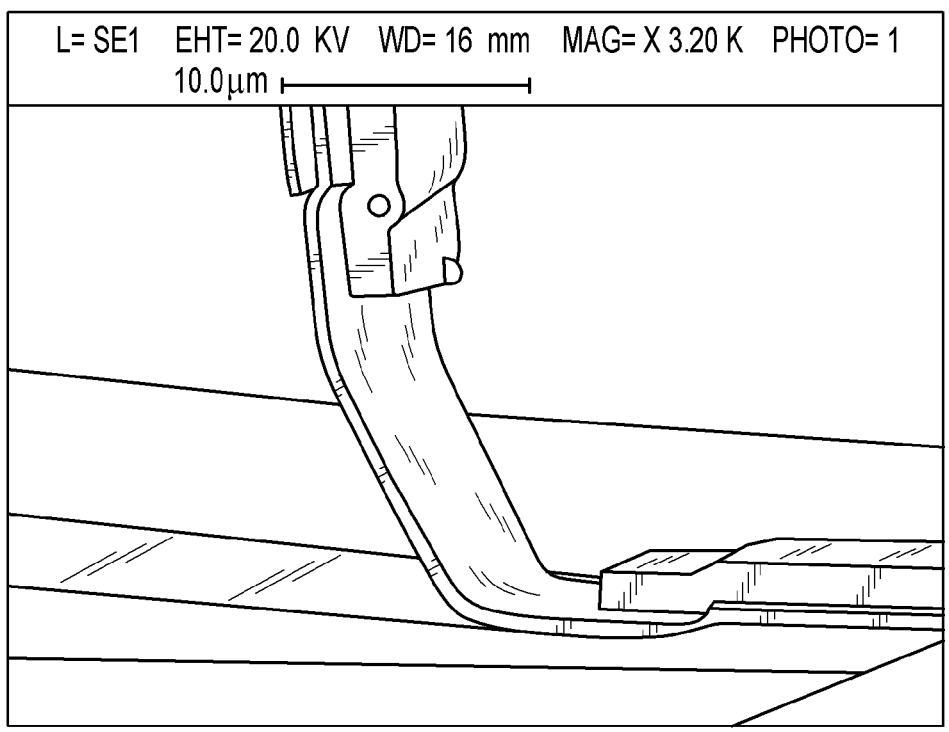
FIGS. 15A and 15B show a plastically deformed Au hinge without and with electroplating, respectively.
Figure 15B:
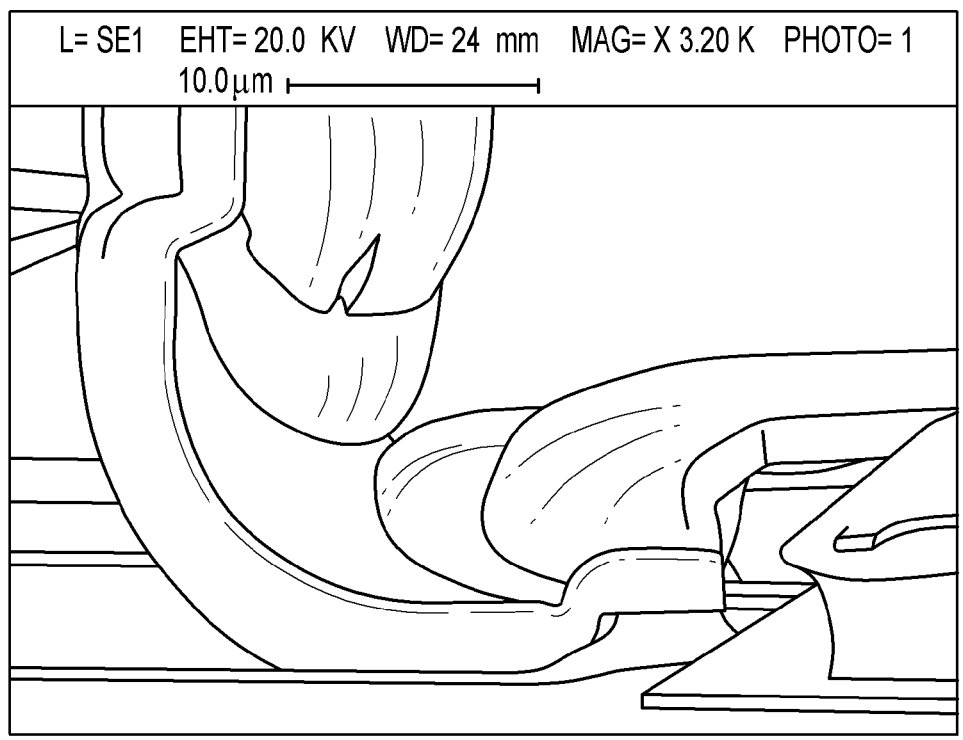
Figure 16:
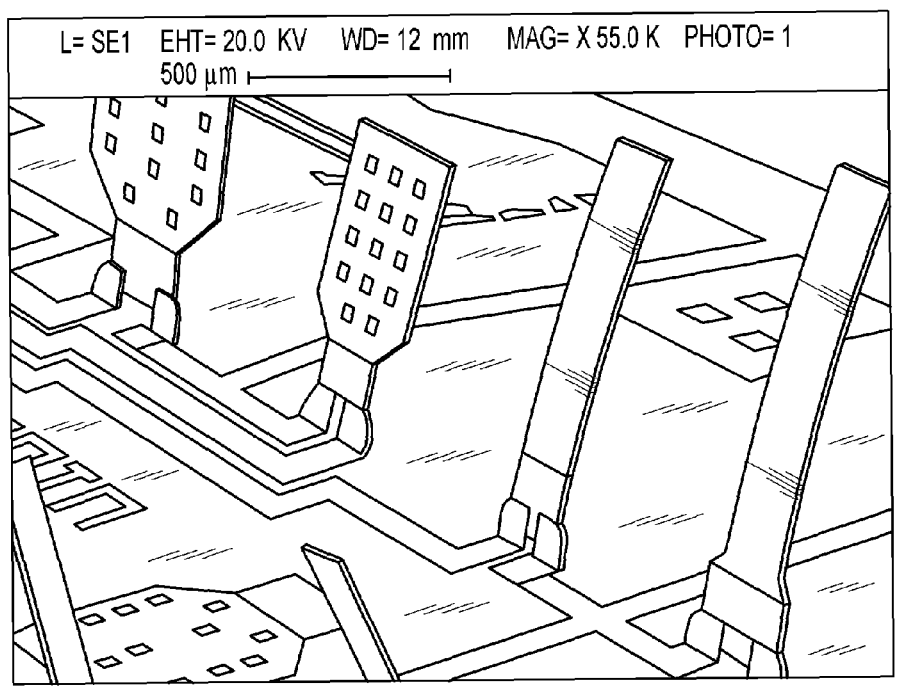
FIG. 16 shows an array of AHCs, having different heights and widths.

SEM images of the hinge are shown in FIG. 15A-15B, showing the difference between a deformed Au hinge with and without Ni plating. An array of AHCs 92 with different vertical cilium and strain gauge geometry is shown in FIG. 16, showing the parallel nature of the preferred fabrication process. Again, it is preferred that overall, the fabrication method does not exceed temperature over 350°Celsius, allowing it to be completed on a skin-like thin film polymer substrate on other substrates. Silicon, glass, and Kapton film, for example, can be used as a substrate for this process. The resistance of devices tested ranges from 1.2 kW to 3.2 kW, and TCR measurement of the as-deposited NiCr film in an exemplary AHC has a value of −25 ppm/° C., which is very small and should not contribute to anemometric effects during airflow testing.

Figure 17:
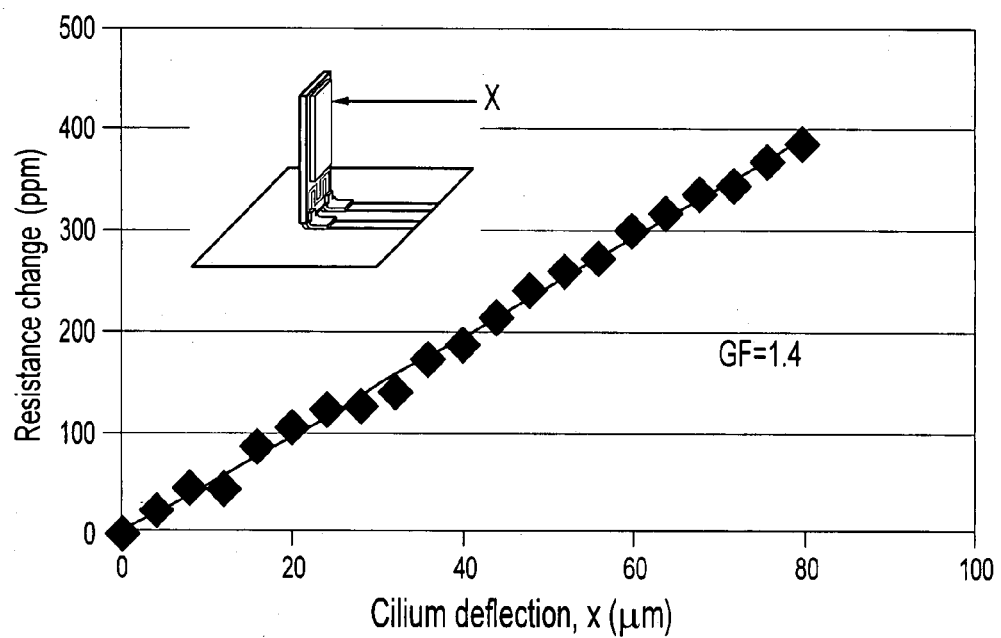
FIG. 17 shows resistance change versus deflection for an 850 μm long and 200 μm wide cilium.

In an exemplary operation of the AHC 92, the resistance change due to external displacement is shown in FIG. 17 for an 850 μm tall vertical cilium. A micromanipulator is used to deflect the distal end of the vertical cilium. The resistance change is measured by a multimeter, and is linear to the beam deflection. The gauge factor GF can be calculated from the slope of the curve, $$GF = \frac{dR/R}{\varepsilon_{Pl}} \quad (5)$$

where dR/R is the percent resistance change, and $e_{PI}$ is the calculated strain from a fixed-free beam (See Eq. (4)) undergoing a deflection x. The plastically deformed hinge, after being plated with approximately 10 μm of Ni, is very rigid. The modulus of elasticity for the nickel is approximately two orders of magnitude larger than polyimide (200 Gpa versus 3.5 Gpa). Therefore, an assumption of a fixed-free cantilever model should be valid. The measured gauge factor for an exemplary strain gauge configuration is about 1.4, which is lower than expected. This could be attributed to the strain gauge not being located at the point of maximum strain.

Several fabricated AHCs were then tested as airflow transducers in a wind tunnel. The airflow with velocity U impinging on the cilium results in a drag force acting normal to the paddle, leading to a moment on the strain gauge $$M = \int_o^l C_D \frac{1}{2}\rho U^2 w y dy \quad (6)$$

where $C_D$ is the drag coefficient, r is the density of air, w and I are the width and length of the cilium. Because strain is proportional to the applied moment, and resistance change is proportional to strain, Equation (6) suggests a quadratic relationship between airflow and resistance change. In addition, by systematically varying the height and width of the cilium, the response can be tailored to different ranges of air velocity. The polarity of resistance change is dependant on the direction of the airflow.

Figure 18:
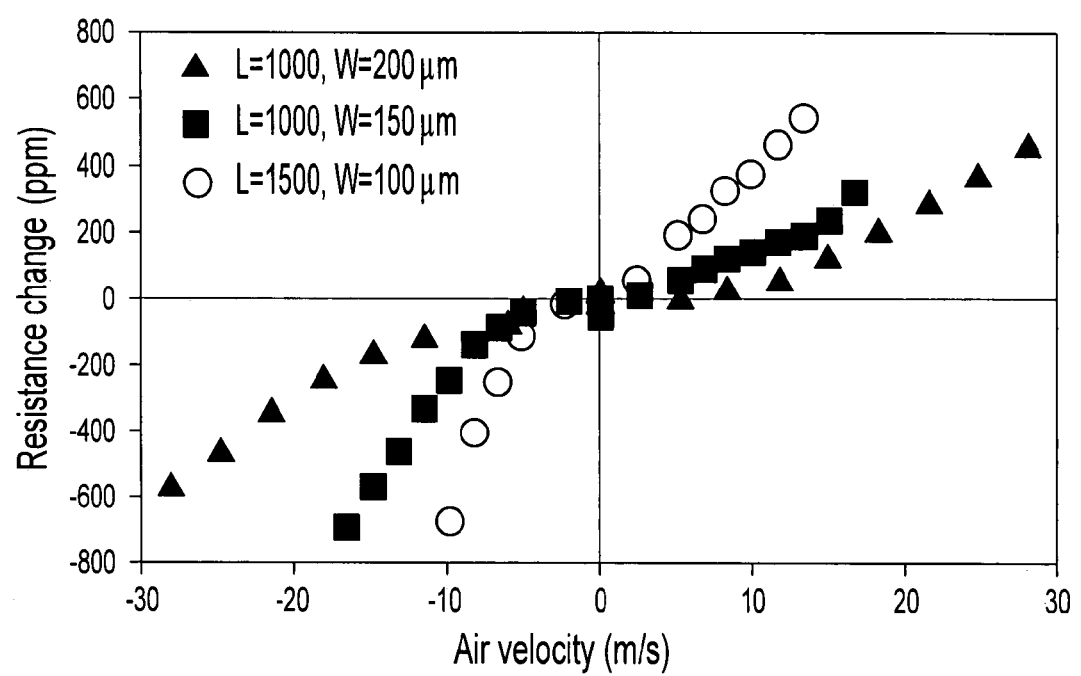
FIG. 18 shows airflow response of AHCs inside a wind tunnel, having various cilium widths and lengths.

The wind tunnel measurement of three AHCs with different cilia geometry is plotted in FIG.18. The AHCs tested were fabricated on a silicon substrate to allow wire bonding to the sample. The AHC with the longest cilium length of 1500 μm is the most sensitive, with dR/R reaching 600 ppm at around 10 m/s. The device with the shortest cilium, even with a greater width, does not have the 600 ppm resistance change until 30 m/s. The sign of resistance change can be indicative of the direction of air velocity. However, the response in various directions does not seem to be symmetrical. This is because it is difficult for the PDMA assembly process to orient the cilium at exactly 90° to the substrate. The characteristic lengths of individual MEMS devices range from 1 μm to 1 mm, although distributed Microsystems containing arrays of devices could have larger overall sizes.

Figure 19:
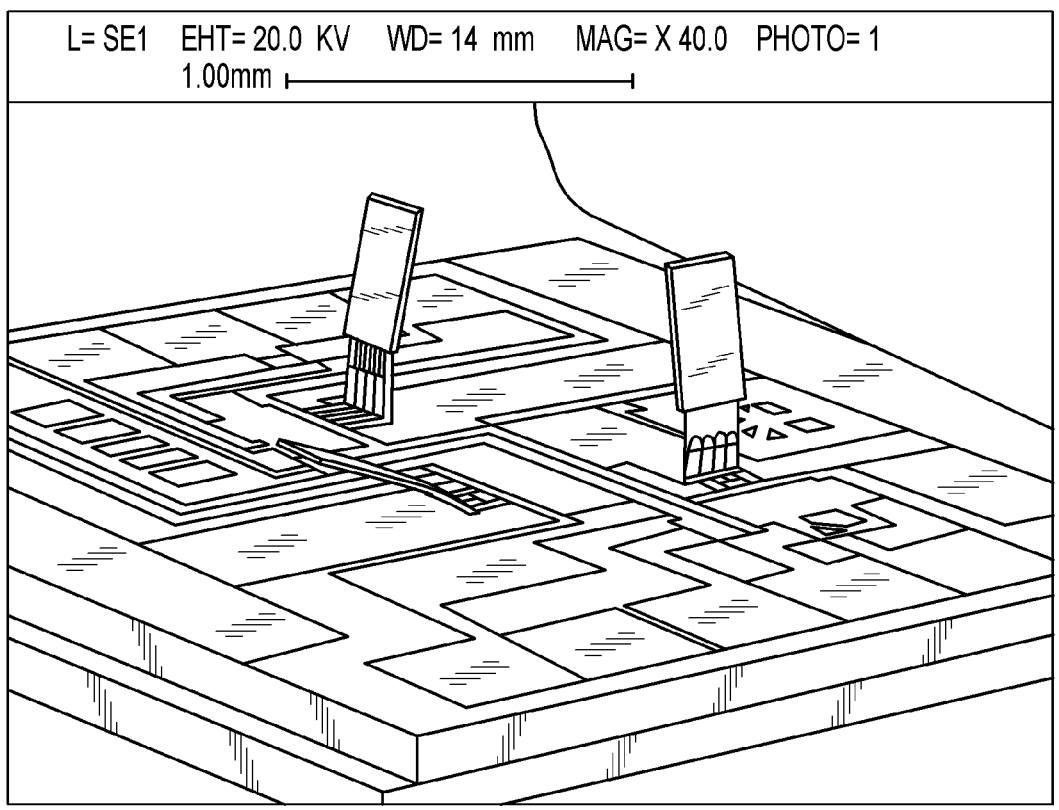
FIG. 19 shows a multidimensional array of AHCs.

The artificial haircell, for example, may be used to realize other sensing modalities, including but not limited to vibration sensing. By varying the geometry and mass of the vertical cilium, the haircell can be made more responsive to inertia forces created by vibration. For example, a three-axis acceleration sensor may be provided, as shown by example in FIG. 19.

Among other flow sensor components, the hot-wire sensor 76 uses an electrical wire placed in the flow field. The wire is heated using ohmic heating and the resistance of the wire (which is a function of temperature) is monitored. Flow imparts forced convection on the wire to induce cooling. The temperature of the wire indicates the flow speed.

Figure 20:
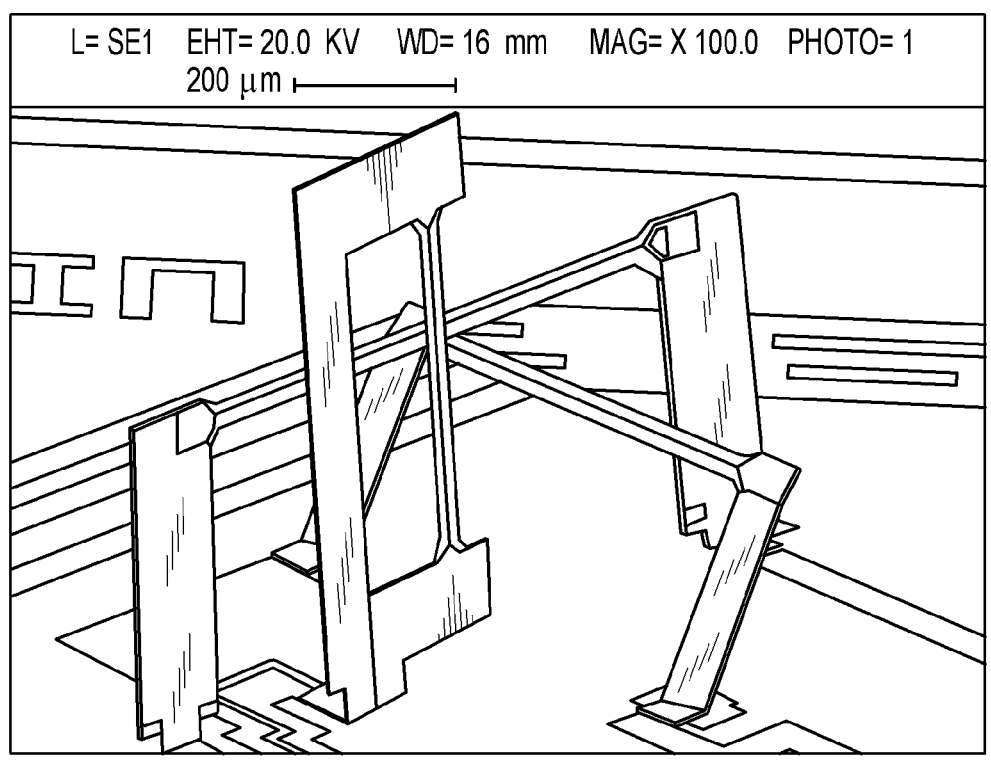
FIG. 20 shows a three-dimensional array of hot wire anemometers, according to an embodiment of the present invention.

Existing hot-wire sensors are all supplied as individual devices. Their sizes are relatively large. Even micromachined hot-wire anemometers are supplied as singular units. They cannot measure the distribution of flow in a distributed field. By contrast, a hot-wire sensor can be made using surface micromachining process and three-dimensional assembly method. It can be made on polymer substrates with large two-dimensional array formats. Examples of hot wire anemometers formed on a substrate and fabrication methods for them are provided in J. Chen and C. Liu, "Development and Characterization of Surface Micromachined, Out-of-Plane Hot-Wire Anemometer," in Journal of Microelectomechanical Systems, Vol. 12, No. 6, December 2003, pp. 979-988, and in J. Chen, J. Zou, and C. Liu, "A Surface Micromachined, Out-of-Plane Anemometer," in Proceedings MEMS, Las Vegas, 2002, pp. 332-335, which are incorporated by reference in its entirety herein. FIG. 20 shows a three-dimensional array of hot-wire anemometers, which can be formed by selecting fabricating individual anemometers and raising them out of plane.

Conventional pressure and shear stress sensors employ a membrane. In the case of a pressure sensor, the diaphragm bends in response to applied pressure difference. In the case of shear stress for measuring fluid stress, the membrane supports a heated hot-wire element. Referring to FIG. 10, the pressure sensor 78 may include, for example, an NiCr strain gauge 120 disposed on a Parylene film 122 forming a raised diaphragm for measuring deflection of the Parylene film in response to pressure. The shear stress sensor 80 may include a raised Parylene membrane with a heated hot-wire element such as a nickel thermoresistor 126 for measuring fluid stress.

Figure 21:
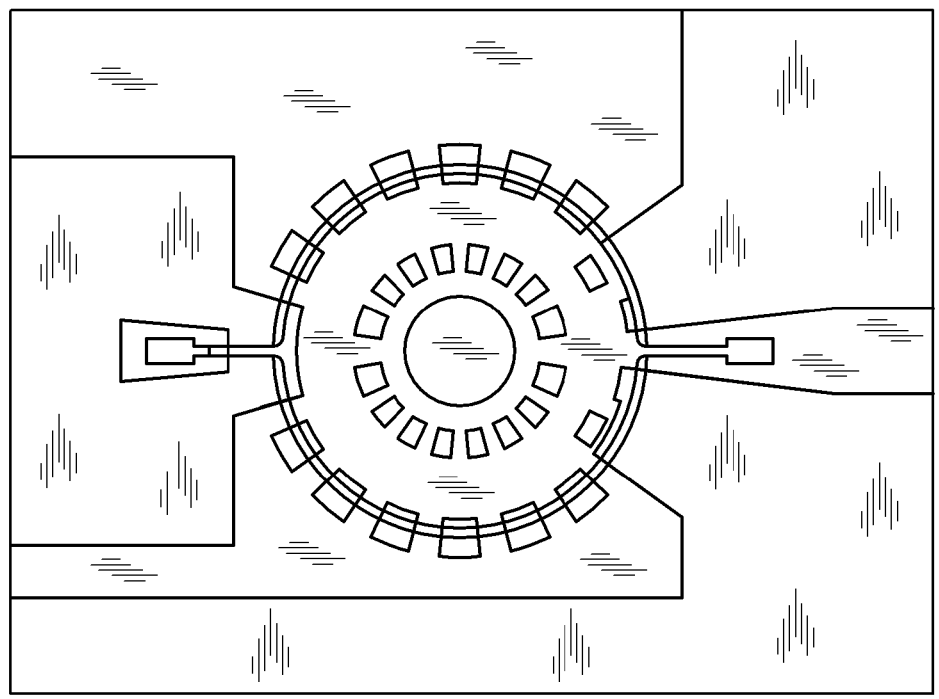
FIG. 21 shows a polymer membrane diaphragm supporting metal leads for a pressure sensor and a shear stress sensor, according to a preferred embodiment of the present invention.

According to another embodiment of the present invention, a microfabrication sequence for a Parylene membrane, shown by example in FIG. 21, with patterned metal on the membrane is provided, in which a preferably polymer membrane diaphragm supports metal leads used for a pressure sensor and for a shear stress sensor. The metal leads can be used for both pressure sensing and shear sensing (temperature sensing). The location preferably determines the principal use of a particular metal lead. For example, the metal leads closer to the center of the membrane may be better located for shear sensing, while the metal leads closer to the edge of the membrane may be better located for pressure sensing.

In an exemplary fabrication process, a photoresist layer is deposited and patterned as a sacrificial layer to define a membrane cavity. A layer of Parylene is deposited, preferably having a thickness in the 0.2 to 5 μm range. A metal thin film is deposited and patterned to form a resistor that can respond to stress (piezoresistor). The gauge factor of such resistors is typically approximately 1-5. Metals that can be used include NiCr (nichrome), Pt, Au, Cu, Al, and others.

Another layer of Parylene is deposited on top of the metal thin film, passivating the resistors and reducing or preventing damage by environmental elements over the long run. The photoresist is removed through spatially placed holes on or around the membrane. The cavity is dried and sealed using one or more of a variety of methods. One exemplary method to seal the cavity is to deposit another thin layer of Parylene. The deposition process is performed at low pressure (e.g., 40 mtorr), and the cavity is therefore sealed under low pressure.

Figure 22:
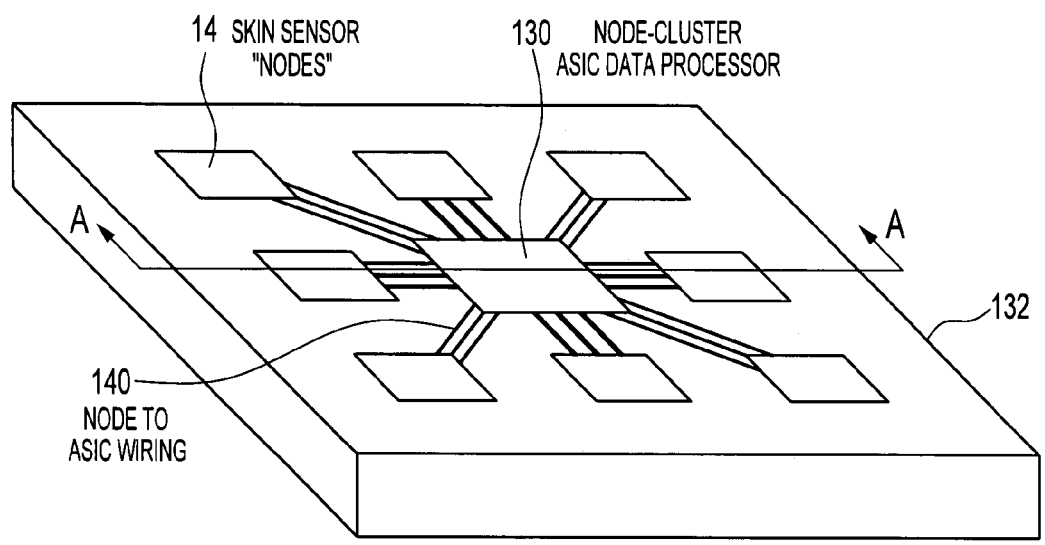
FIG. 22 shows an exemplary cluster of sensor nodes disposed about a data processor.

In another embodiment of the present invention, exemplary methods are provided for integrating silicon chips (containing signal processing functions such as amplification, multiplexing, and analog-to-digital conversion) with a polymer sensor chip (with tactile or flow sensing components) and within the fabrication flow. FIG. 22 shows an overview of a skin architecture showing a cluster of sensor nodes connected to a local cluster processor.

Figure 23A:
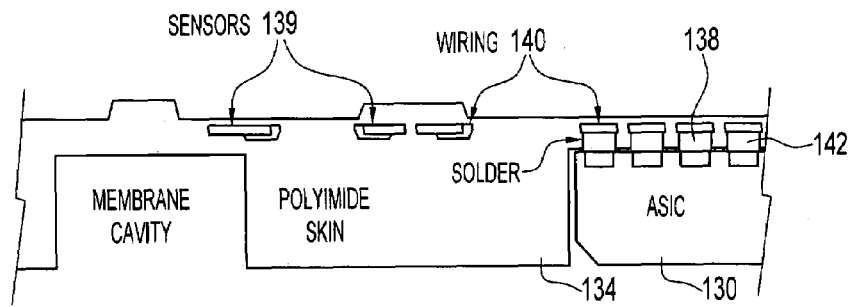
FIGS. 23A-23C show methods for placing a data processor on a polymer substrate.

A first method includes bonding a silicon chip, such as a commercially obtained chip 130 (e.g., ADC chip with internal clock from National Semiconductors) onto a polymer sensor skin. 132. The chip may be, for example, an application-specific IC chip. A schematic diagram of this bonding approach is shown in FIG. 23A. In a preferred bonding process, a blank slot 134 on the back surface of the sensor skin 132 is opened for the microelectronic chip 130 to rest. A through-wafer electrical interconnect 138 is provided so that the silicon chip 130 rests on the backplane and not the front plane, where the chip may interface with surface roughness. Chip-to-polymer metal bonding technology using low melting temperature metal thin films provides flip-chip bonding.

The assembly is repeated across the skin 132 with additional circuits that handle multiple clusters for a distributed system. FIG. 23A shows an embedded sensor 139 and wiring 140 with an ASIC flip chip 130 bonded to backside vias 138 with solder bumps 142.

Figure 23B:
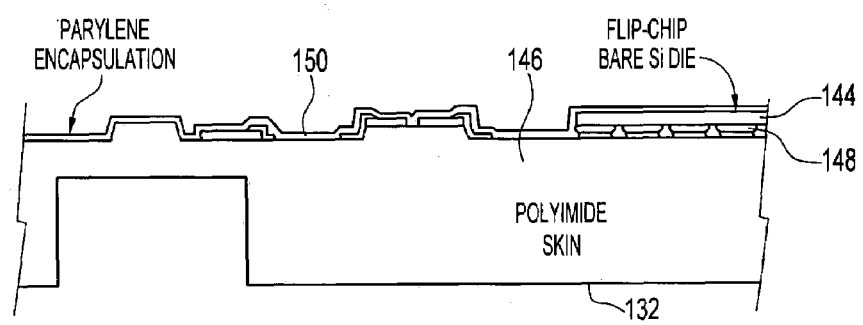
Figure 24:
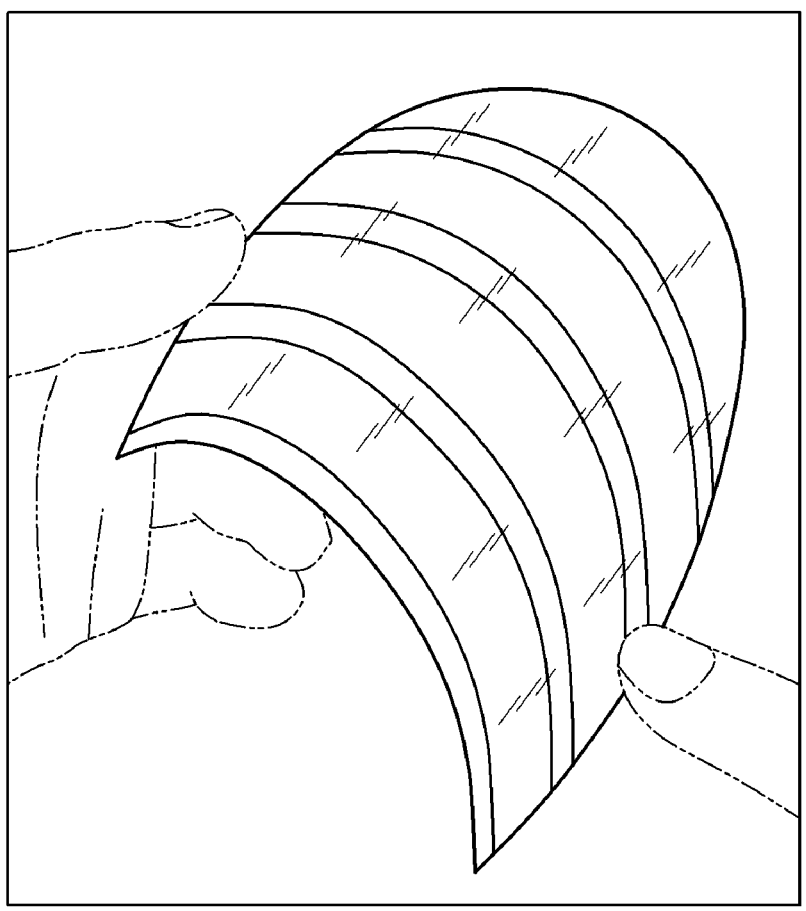
FIG. 24 shows a flexible silicon chip.
Figure 25A:
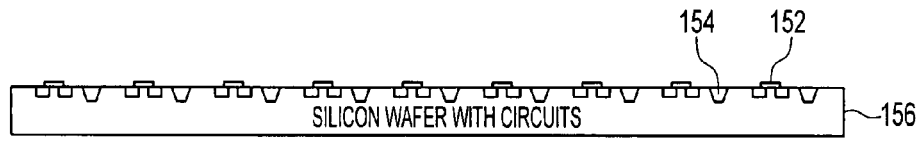
FIG. 25 shows steps in an exemplary process for forming an elastomer skin with embedded silicon islands.
Figure 25B:
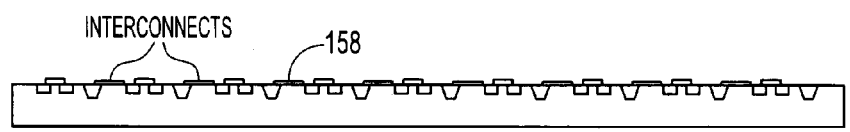
Figure 25C:
Figure 25D:
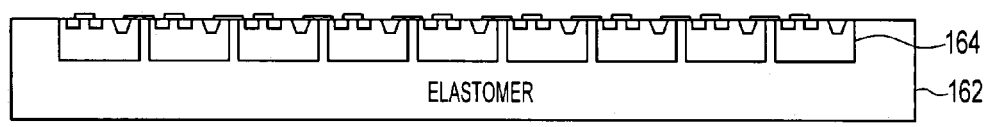
Figure 25E:
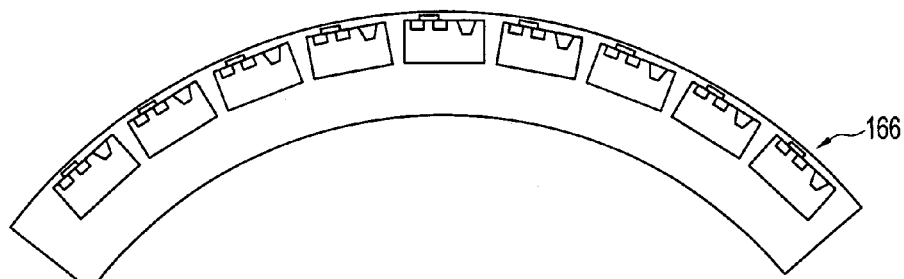

A second method, shown by example in FIG. 23B, includes thinning a semiconductor wafer 144 that contains analog/digital electronics at the top surface 146 to the point that the semiconductor wafer becomes flexible and yet still maintains electronics functionalities. For example, a chip having a small die size (e.g., less than 1 cm$^2$) with thickness on the order of 10-30 micrometers, may be used. An exemplary thinned silicon wafer is shown in FIG. 24. The silicon dies flex with the polymer substrate 132 and therefore preserve the mechanical flexibility. As shown in FIG. 23B, thin dies may be flip-chip bonded to bonding sites 148 on polymer sensor skin 132. The chip-to-polymer electrical connection may be achieved, for example, using low temperature metal reflow. The top surface 146 can be further protected and mechanically enhanced using conformal chemical vapor deposition of a plastic 150 such as Parylene, which is stress free, relatively soft, and does not damage the microelectronics or the sensor.

Figure 23C:
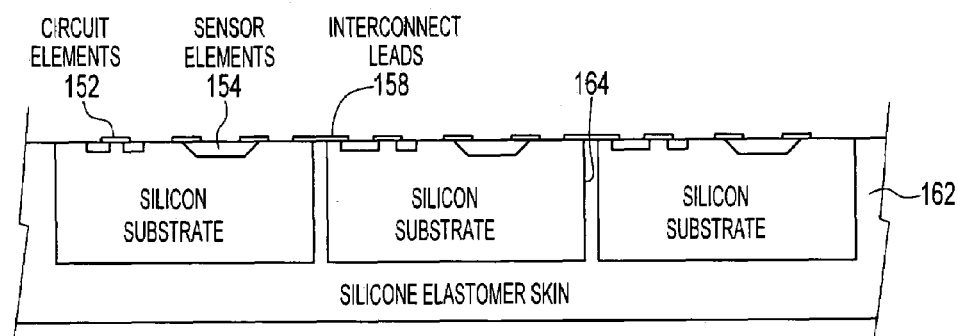

In a third method, shown by example in FIG. 23C and FIG. 25, both circuit elements 152 and sensor elements 154 are built on a silicon wafer 156 first. The sensors 154 are preferably formed on the wafer 156 after the circuit elements 152 are formed (step (a) in FIG. 25). This is feasible since the sensor elements 154 preferably can be formed under low processing temperatures. An exemplary method uses a silicon wafer 156 having preformed circuit elements, on which the sensor elements 154 are formed. Such silicon wafers 156 may contain, for example, op-amps, multiplexors, and/or A/D conversion functions.

Post-process steps are performed to build interconnect wires 158 (step (b)) and the tactile or flow sensor elements 154. Next, the backside of the wafer 156 is patterned and etched (step (c)) to form trenches 160. An elastomer precursor 162 is poured and cured (step (d)), to encase resulting silicon islands 164 in a elastomer back-filled skin. The front surface of the skin can be further protected, for example, by depositing a protective layer such as Parylene using chemical vapor deposition. These steps provide a flexible sensor chip 166, as shown flexed at step (e).

While specific embodiments of the present invention have been shown and described, it is to be understood that other modifications, substitutions, and alternatives will be apparent to those of ordinary skill in the art. Such modifications, substitutions, and alternatives can be made without departing from the spirit and scope of the present invention, which should be determined from the appended claims.

Various features of the invention are set forth in the appended claims.

What is claimed is:

1. A microfabricated pressure sensor comprising:
   a polymer film providing a raised diaphragm, the raised diaphragm being disposed on a flexible polymer substrate, said diaphragm being configured to bend in response to an applied pressure difference;
   a strain gauge of a conductive material coupled to a surface of the raised diaphragm and to at least one of the substrate and a piece rigidly connected to the substrate.

2. A microfabricated shear stress sensor comprising:
   a polymer film providing a raised membrane, the raised membrane being disposed on a flexible polymer substrate;
   a heated hot-wire element disposed on a surface of the membrane for sensing fluid stress.

3. The pressure sensor of claim 1, wherein the surface of the raised diaphragm is exposed.

4. The pressure sensor of claim 1, wherein the strain gauge comprises a nichrome film formed on the surface of the raised diaphragm.

5. The pressure sensor of claim 1, wherein the polymer film comprises Parylene.

6. The pressure sensor of claim 5, wherein the substrate comprises polyimide.

7. The pressure sensor of claim 1, further comprising:
   a plurality of additional pressure sensors disposed in an array on a surface of the substrate, each of said plurality of pressure sensors comprising:
      an additional polymer film providing an additional raised diaphragm, the additional raised diaphragm being disposed on the substrate; and
      an additional strain gauge of a conductive material coupled to a surface of the additional raised diaphragm and to the substrate.

8. The pressure sensor of claim 7, wherein the array is two-dimensional.

9. The shear stress sensor of claim 2, wherein the surface of the raised membrane is exposed.

10. The shear stress sensor of claim 2, wherein the heated hot-wire element comprises a nickel thermoresistor formed on the surface of the raised membrane.

11. The shear stress sensor of claim 2, wherein the polymer film comprises Parylene.

12. The shear stress sensor of claim 11, wherein the substrate comprises polyimide.

13. The shear stress sensor of claim 2, further comprising:
a plurality of additional shear stress sensors disposed in an array on a surface of the substrate, each of said plurality of shear stress sensors comprising:
   an additional polymer film providing an additional raised membrane, the additional raised membrane being disposed on the substrate; and
   an additional heated hot-wire element disposed on a surface of the additional raised membrane.

14. The shear stress sensor of claim 13, wherein the array is two-dimensional.

15. A fluid flow sensing device comprising:
an array of sensor nodes disposed on a flexible polymer substrate, each of the sensor nodes comprising at least one microfabricated pressure sensor and at least one microfabricated shear stress sensor;
wherein each of the at least one microfabricated pressure sensor comprises a first polymer film providing a raised diaphragm, the raised diaphragm being disposed on the flexible polymer substrate, said raised diaphragm being configured to bend in response to an applied pressure difference, and a strain gauge of a conductive material coupled to a surface of the raised diaphragm and to at least one of the substrate and a piece rigidly connected to the substrate;
wherein each of the at least one microfabricated shear stress sensor comprises a second polymer film providing a raised membrane, the raised membrane being disposed on the flexible polymer substrate, and a heated hot-wire element disposed on a surface of the membrane for sensing fluid stress.

16. The fluid flow sensing device of claim 15, wherein the array is two-dimensional.

17. The fluid flow sensing device of claim 15, wherein the first polymer film and the second polymer film comprise Parylene.

18. The fluid flow sensing device of claim 17, wherein the flexible polymer substrate comprises polyimide.

* * * * *

UNITED STATES PATENT AND TRADEMARK OFFICE
CERTIFICATE OF CORRECTION

PATENT NO. : 7,509,869 B2
APPLICATION NO. : 11/880134
DATED : March 31, 2009
INVENTOR(S) : Liu et al.

Page 1 of 1

It is certified that error appears in the above-identified patent and that said Letters Patent is hereby corrected as shown below:

In the Specification:

Col. 13, line 54      After "coefficient," please delete "r" and insert --$\rho$-- in its place.

Col. 13, line 55      Before "are the width" please delete "I" and insert --$l$-- in its place.

Signed and Sealed this

Twenty-ninth Day of September, 2009

David J. Kappos
*Director of the United States Patent and Trademark Office*